United States Patent
Li

(10) Patent No.: US 10,709,725 B2
(45) Date of Patent: Jul. 14, 2020

(54) GEMCITABINE PROTIDE HYPOXIA-ACTIVATED PRODRUG AND APPLICATION THEREOF

(71) Applicant: JIANGSU QIANZHIKANG BIOLOGICAL MEDICINE SCIENCE AND TECHNOLOGY CO., LTD, Nantong (CN)

(72) Inventor: Fei Li, Nantong (CN)

(73) Assignee: JIANGSU QIANZHIKANG BIOLOGICAL MEDICINE SCIENCE AND TECHNOLOGY CO., LTD, Nantong (CN)

( * ) Notice: Subject to any disclaimer, the term of this patent is extended or adjusted under 35 U.S.C. 154(b) by 0 days.

(21) Appl. No.: 16/322,936

(22) PCT Filed: Aug. 3, 2017

(86) PCT No.: PCT/CN2017/095794
§ 371 (c)(1),
(2) Date: Feb. 2, 2019

(87) PCT Pub. No.: WO2018/028494
PCT Pub. Date: Feb. 15, 2018

(65) Prior Publication Data
US 2019/0192547 A1 Jun. 27, 2019

(30) Foreign Application Priority Data

Aug. 9, 2016 (CN) ........................... 2016 1 0649914
Jul. 25, 2017 (CN) ........................... 2017 1 0610509

(51) Int. Cl.
| C07H 19/10 | (2006.01) |
| A61K 31/7068 | (2006.01) |
| A61P 35/00 | (2006.01) |
| C07H 1/00 | (2006.01) |
| C07H 1/02 | (2006.01) |

(52) U.S. Cl.
CPC .......... *A61K 31/7068* (2013.01); *A61P 35/00* (2018.01); *C07H 1/00* (2013.01); *C07H 1/02* (2013.01); *C07H 19/10* (2013.01)

(58) Field of Classification Search
None
See application file for complete search history.

(56) References Cited

FOREIGN PATENT DOCUMENTS

| CN | 105001291 A | 10/2015 |
| CN | 105792845 A | 7/2016 |
| CN | 106279321 A | 1/2017 |

OTHER PUBLICATIONS

Slusarczyk et al.—Journal of Medicinal Chemistry, vol. 57, pp. 1531-1542, 2014 (Year: 2014).*
Zhi-Wei Guo et. al., Selective Protection of 2',2'-Difluorodeoxycytidine (Gemcitabine), The Journal of Organic Chemistry, Oct. 6, 1999, vol. 64, No. 22, pp. 8319-8322.
Christopher P. Guise et. al., Bioreductive prodrugs as cancer therapeutics: targeting tumor hypoxia, Chinese Journal of Cancer, 2014, vol. 33 Issue 2, pp. 80-86.
Adrian L.Harris, Hypdxia—A Key Regulatory Factor in Tumour Growth, Nature Reviews Cancer, Jan. 2002, vol. 2, pp. 38-47.
Mitesh J. Borad et. al., Randomized Phase II Trial of Gemcitabine Plus TH-302 Versus Gemcitabine in Patients With Advanced Pancreatic Cancer, Journal of Clinical Oncology, May 1, 2015, vol. 33, No. 13, pp. 1475-1482.
Magdalena Slusarczyk et. al., Application of ProTide Technology to Gemcitabine: A Successful Approach to Overcome the Key Cancer Resistance Mechanisms Leads to a New Agent (NUC-1031) in Clinical Development, Journal of Medicinal Chemistry, Jan 28, 2014, vol. 57, No. 4, pp. 1531-1542.

* cited by examiner

*Primary Examiner* — Traviss C McIntosh, III
(74) *Attorney, Agent, or Firm* — Bayramoglu Law Offices LLC

(57) ABSTRACT

A gemcitabine ProTide hypoxic-activated prodrug and a use thereof in the preparation of a medicament for treating tumors. The general structural formula thereof is formula (A), wherein: one of R1 and R2 is a hypoxic-activated group of —C(R3R4)ArNO2, and the other is an alkyl group of 1 to 6 carbon atoms, a phenyl group or —CH2Ar, wherein R3 and R4 are —H or a methyl group, and —Ar is an aromatic ring compound. The gemcitabine ProTide hypoxic-activated prodrug described in the present invention has a stronger cytotoxicity under a hypoxic condition, has excellent anti-tumor effects and is very safe; the present invention can be used along with other anti-tumor drugs to exert a better anti-tumor activity, and can be used in the preparation of a medicament for treating tumors.

14 Claims, 2 Drawing Sheets

GEMCITABINE PROTIDE HYPOXIA-ACTIVATED PRODRUG AND APPLICATION THEREOF

CROSS REFERENCE TO RELATED APPLICATIONS

This application is the national phase entry of International Application No. PCT/CN2017/095794, filed on Aug. 3, 2017, which is based upon and claims priority to Chinese Patent Application No. 201610649914.X, filed on Aug. 9, 2016, and Chinese Patent Application No. 201710610509.1, filed on Jul. 25, 2017, the entire contents of which are incorporated herein by reference.

TECHNICAL FIELD

The present invention belongs to the field of pharmacy, and provides a gemcitabine ProTide hypoxic-activated prodrug and a use thereof.

BACKGROUND

Gemcitabine is a nucleoside anti-tumor drug. The mechanism of action of this drug is to antagonize nucleotide metabolism. After intracellular triphosphorylation in vivo, gemcitabine specifically interferes with nucleic acid metabolism and prevents cell division and reproduction by inhibiting the synthesis of deoxynucleoside triphosphate (dNTPs), interfering with cell replication by being incorporated into DNA or RNA molecules, competitively inhibiting DNA polymerase, and the like, thus eventually causing the death of tumor cells. Nucleoside anti-tumor drugs are prone to drug resistance, but ProTide prodrugs thereof can reduce the occurrence of drug resistance and have a good anti-tumor effect, among which a gemcitabine ProTide prodrug NUC-1031 has been clinically studied (Journal of Medical Chemistry 2014, 57, 1531-1542). However, ProTide prodrugs cannot reduce the toxic and side effects of drugs on non-tumor tissues.

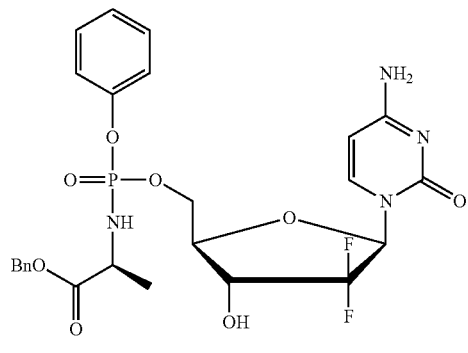

NUC-1031

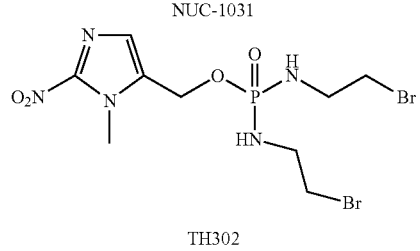

TH302

With the rapid growth of tumors, some tumor tissues are farther and farther away from the nearest blood vessel, and oxygen supply is insufficient, resulting in tumor hypoxia (Nature review cancer 2002, 2: 38-47). Traditional anti-tumor drugs have good lethality to tumors near blood vessels, but have limited effects on tumors in hypoxic regions. Tumor hypoxic-activated prodrugs can specifically release anti-tumor active constituents in tumor hypoxic regions, thus killing tumors in the hypoxic regions (Chinese Journal of Cancer 2014, 33: 80-86). Hypoxic-activated prodrugs have a tumor targeting property, thus having a better safety performance, and a better anti-tumor effect when used in combination with traditional anti-tumor drugs, among which TH302 has been clinically studied and has a good therapeutic effect on pancreatic cancer (Journal of Clinical Oncology 2015, 33, 1475-1482).

SUMMARY

Technical Problem

The present invention provides a gemcitabine ProTide hypoxic-activated prodrug and a use thereof. The prodrug has a stronger cytotoxicity under a hypoxic condition, has excellent anti-tumor effects and is very safe, can be used along with traditional anti-tumor drugs to exert a good anti-tumor activity at a small dose, and can be used in the preparation of a medicament for treating tumors.

Technical Solution

The chemical structural formula of the gemcitabine ProTide hypoxic-activated prodrug is:

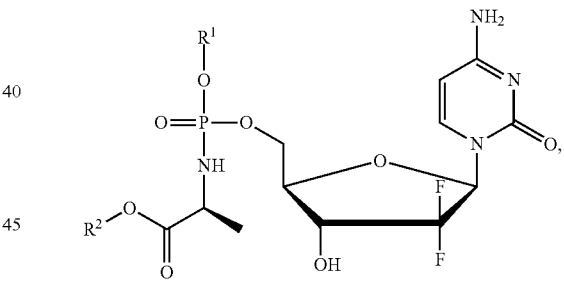

wherein one of $R^1$ and $R^2$ is a hypoxic-activated group of —$C(R^3R^4)ArNO_2$, the other is an alkyl group of 1 to 6 carbon atoms, a phenyl group or —$CH_2Ar$, $R^3$ and $R^4$ are —H or a methyl group, and —Ar is an aromatic ring compound.

As a preferred scheme, for the gemcitabine ProTide hypoxic-activated prodrug, the structure of $R^1$ is:

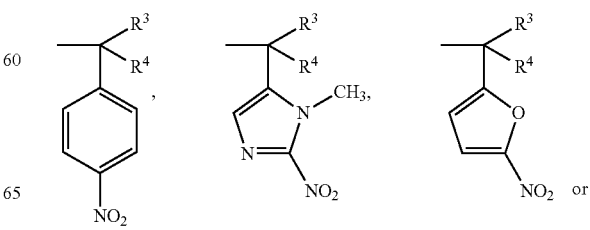

or

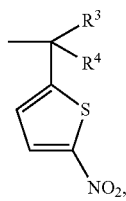

$R^2$ is an alkyl or benzyl group of 1 to 6 carbon atoms, $R^3$ is —H or a methyl group, and $R^4$ is a methyl group.

As a preferred scheme, for the gemcitabine ProTide hypoxic-activated prodrug, $R^1$ is a phenyl group, and the structure of $R^2$ is:

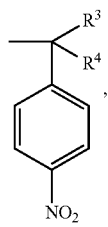, 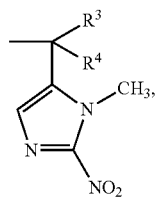, 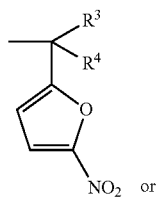 or

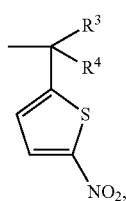

$R^3$ is —H or a methyl group, and $R^4$ is a methyl group.

As a preferred scheme, for the gemcitabine ProTide hypoxic-activated prodrug, the structure of $R^1$ is:

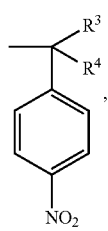, 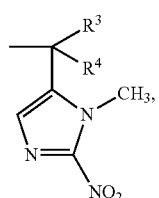, 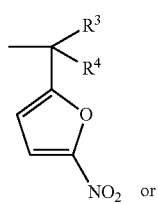 or

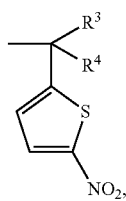

$R^2$ is an alkyl or benzyl group of 1 to 6 carbon atoms, $R^3$ and $R^4$ are —H.

As a preferred scheme, for the gemcitabine ProTide hypoxic-activated prodrug, $R^1$ is —CH$_2$Ar, —Ar is a benzene ring with an electron donating group, and the structure of $R^2$ is:

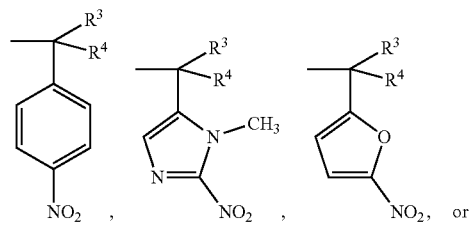

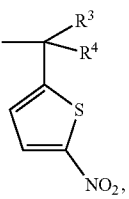

$R^3$ is —H or a methyl group, and $R^4$ is a methyl group.

As a preferred scheme, the structure of the gemcitabine ProTide hypoxic-activated prodrug is as follows:

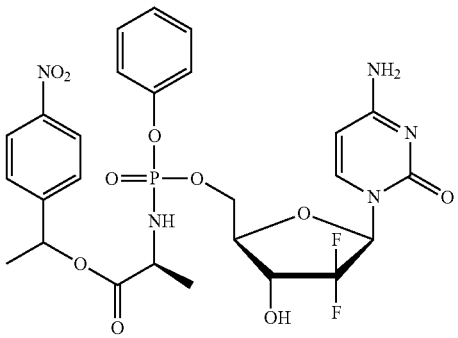

001

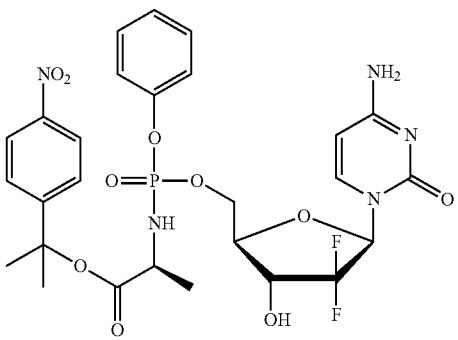

002

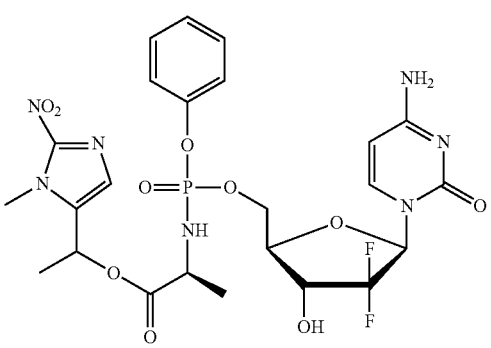

003

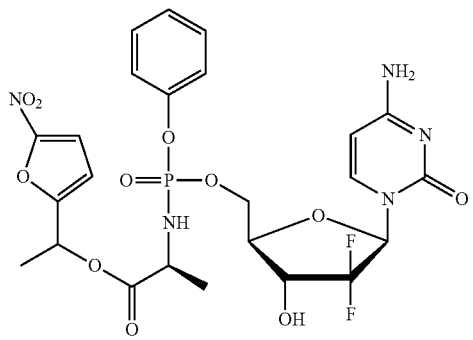
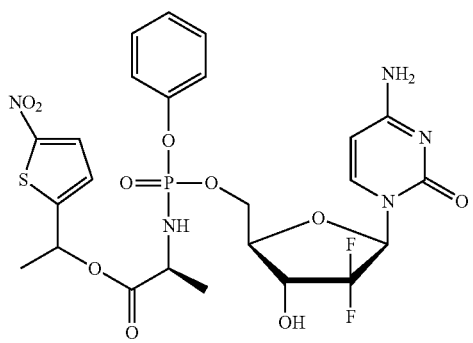
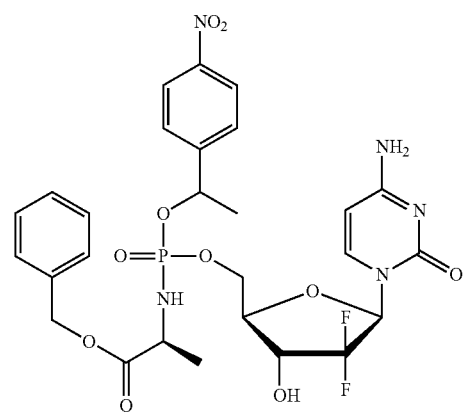
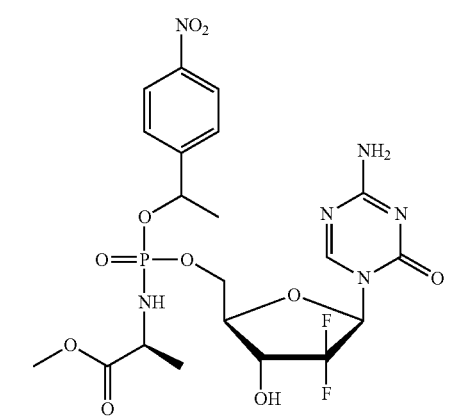
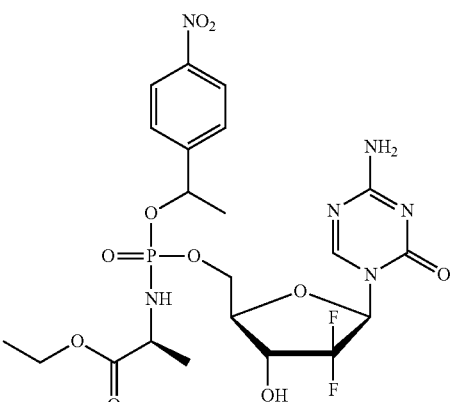
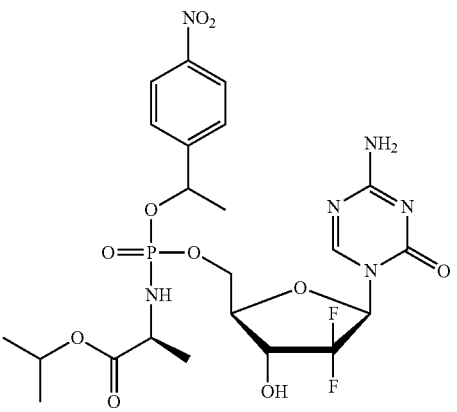
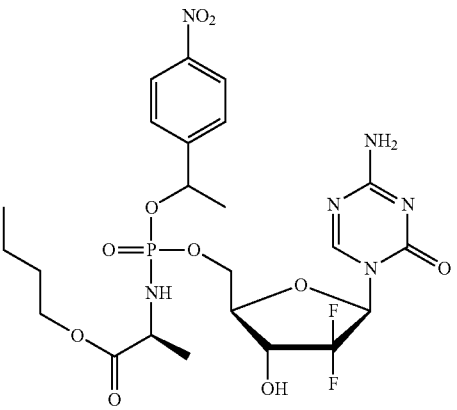
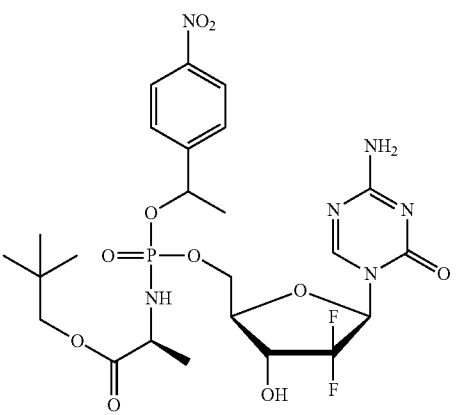

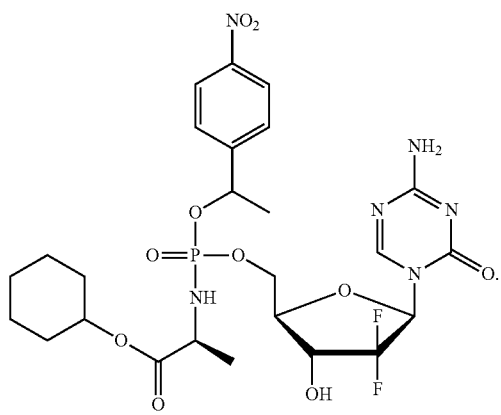
012
As a preferred scheme, the structure of the gemcitabine ProTide hypoxic-activated prodrug is as follows:
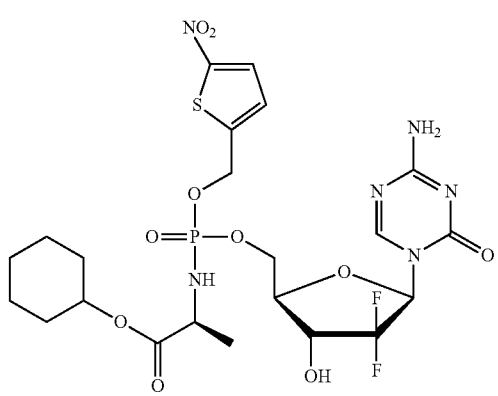
013
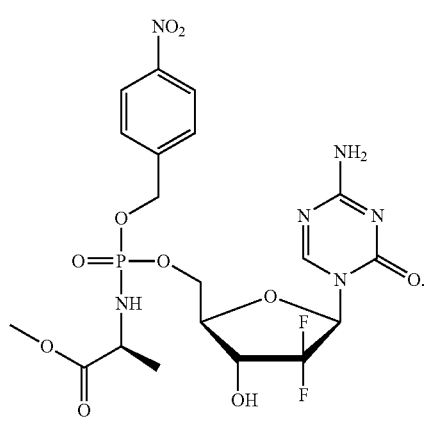
014
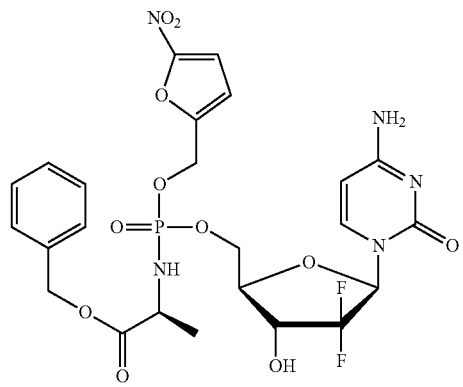
015
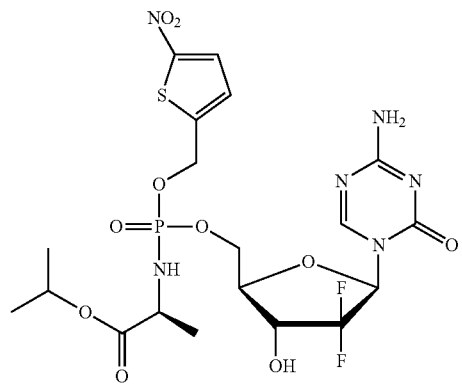
016
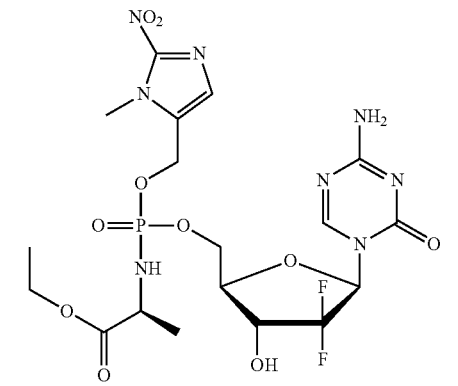
017
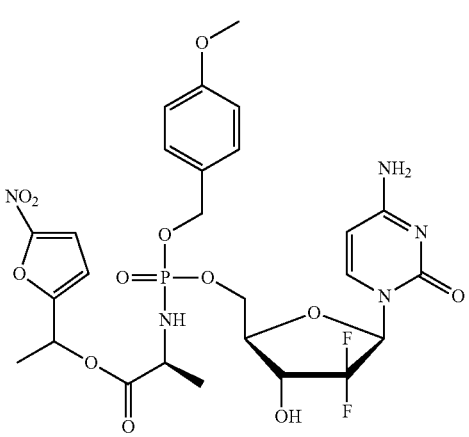
018

-continued

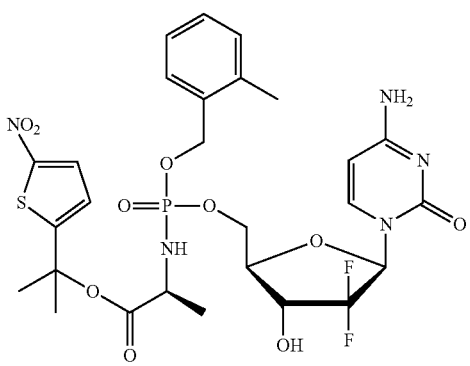

019

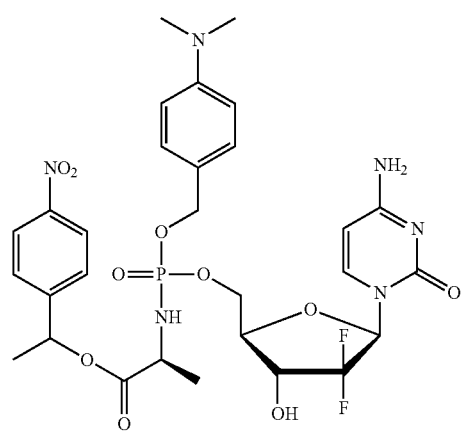

020

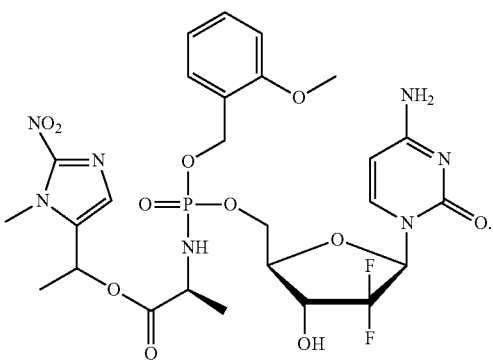

021

A use of the above compound or pharmaceutically acceptable salt thereof in the preparation of a medicament for treating tumors.

A use of a composition of the above compound or pharmaceutically acceptable salt thereof and gemcitabine hydrochloride in the preparation of a medicament for treating tumors.

A medicament for treating tumors, of which the effective component being the above gemcitabine ProTide hypoxic-activated prodrug or pharmaceutically acceptable salt thereof.

A medicament for treating tumors, of which the effective component being the composition of the above gemcitabine ProTide hypoxic-activated prodrug or pharmaceutically acceptable salt thereof and gemcitabine hydrochloride.

It should be pointed out that our research found that the cytotoxicity of compounds 001-021 under a hypoxic condition was significantly higher than that under a normal oxygen condition. The cytotoxicity of a target compound (e.g., compound 022) obtained by introducing a hypoxic-activated group into an amino position of gemcitabine ProTide prodrug NUC-1031 under a hypoxic condition was not significantly different from that under a normal oxygen condition (see Table 1). It indicated that the introduction position of the hypoxic-activated group was specific for maintaining the hypoxic-activated function of drugs.

It should also be pointed out that our research found that when $R^2$ was a hypoxic-activated group, if $R^3$ and $R^4$ were both H (such as compound 023), the cytotoxicity of the target compound under a hypoxic condition was not significantly different from that under a normal oxygen condition (see Table 1), while when $R^1$ was a hypoxic-activated group, if $R^3$ and $R^4$ were both H (such as compounds 013-017), the cytotoxicity of the target compound under a hypoxic condition was significantly higher than that under a normal oxygen condition (see Table 1).

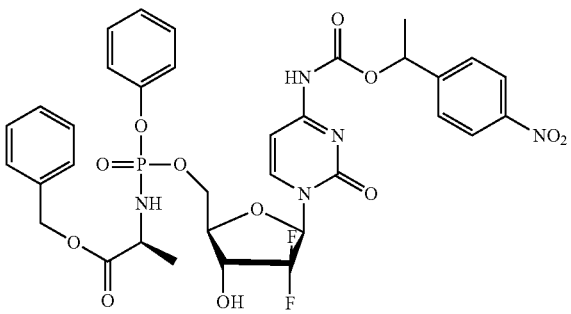

022

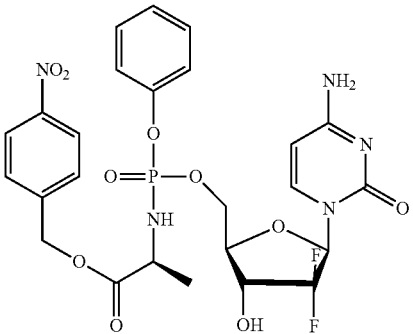

023

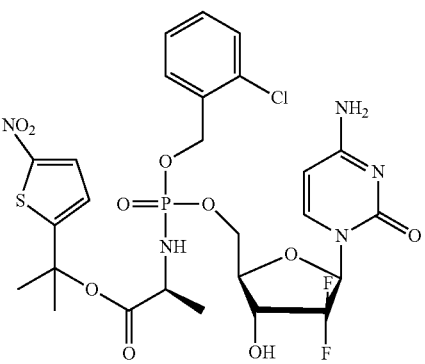

024

When $R^1$ was a hypoxic-activated group, $R^2$ was —CH$_2$Ar, and Ar was a phenyl group with an electron donating group, the target compound showed a stronger cytotoxicity under a hypoxic condition (such as compounds 018-021); when Ar was a phenyl group having no substituent group or having an electron with-drawing group (such as compound 024), the cytotoxicity of the target compound under a hypoxic condition differed slightly from that under a normal oxygen condition.

Taking compound 001 as an example, the anti-tumor effect and safety performance of the target compound were investigated. The target compound showed a significant anti-tumor growth effect (see FIG. 1 and FIG. 2). At 4 times of treatment dose, compared with a control group, there was no significant difference in animal weight, indicating that the target compound had good safety performance (see FIG. 3). Combined use with traditional anti-tumor drugs such as gemcitabine can generate better anti-tumor effect (see FIG. 2).

Advantageous Effect

The gemcitabine ProTide hypoxic-activated prodrug of the present invention has a small cytotoxicity in a normal oxygen environment and strong cytotoxicity under a hypoxic condition, therefore, the gemcitabine ProTide hypoxic-activated prodrug can specifically play an anti-tumor effect on tumors in tumor hypoxic regions, reduce toxic and side effects on other tissues, has an excellent anti-cancer effect and good safety performance, can be used together with traditional anti-tumor drugs such as gemcitabine to generate a good anti-tumor effect at a small dose, and can be used for preparing medicaments for treating tumors. Further research finds that at 4 times of effective dose, the gemcitabine ProTide hypoxic-activated prodrug provided by the present invention has no obvious toxic effect increase compared with low dose.

DETAILED DESCRIPTION OF THE EMBODIMENTS

Figure 1:
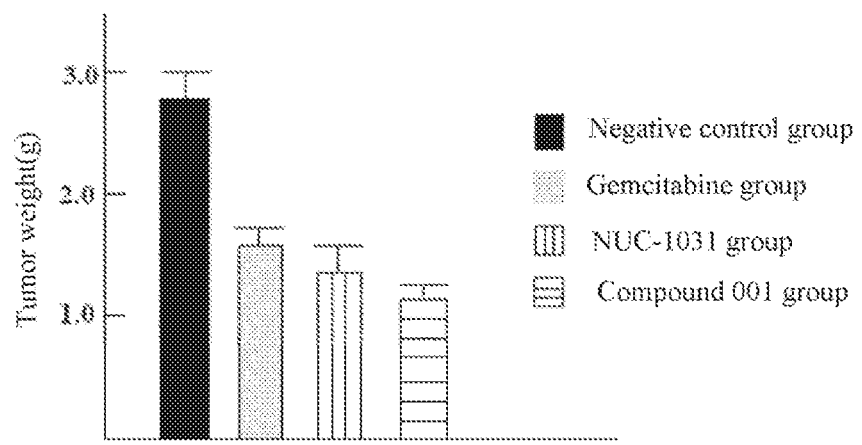
FIG. 1 is a schematic diagram of a growth inhibition effect of a target compound 001 on orthotopic transplantation tumor of human BxPC-3 nude mice. After administration, the pancreatic cancer tumor tissue quality of nude mice in an experimental group (compound 001) was significantly lower than that of a gemcitabine group and an NUC-1031 group, indicating a better tumor growth inhibition effect.

The following embodiments enable those skilled in the art to fully understand the present invention, but do not limit the present invention in any way.

Embodiment 1: Synthesis of Target Compounds 001-021

Synthesis of compound 001

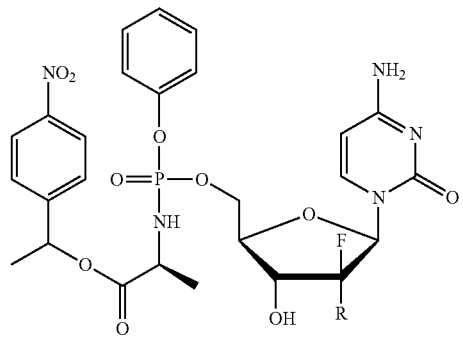

Synthesis of 3'-O-(t-butyloxycarboryl) gemcitabine

Synthesis route (method reference, The Journal of Organic Chemistry, 1999, 64: 8319-8322):

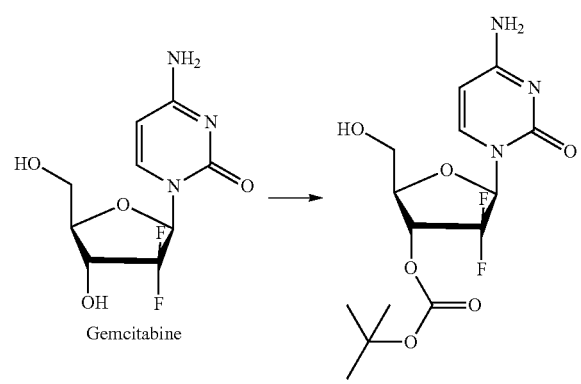

Experimental operation: stir gemcitabine (0.60 g, 2 mmol), $Na_2CO_3$ (1.06 g), 40 mL dioxane, 40 mL water, di-tert-butyl dicarbonate ester (DBDC, 0.44 g, 2 mmol) at room temperature for 48 h; add 20 mL water, extract with 2×300 mL ethyl acetate, dry with $Na_2SO_4$, and perform vacuum concentration; perform flash column chromatography on ($CH_2Cl_2$-ethyl acetate-EtOH 1:1:0.02) to obtain 3'-O—(N-t-butyloxycarboryl) gemcitabine (0.60 g). $^1H$ NMR (DMSO-d6, 300 MHz) δ(ppm): 7.64 (d, 1H) 7.40 (d, 2H), 6.21 (t, 1H), 5.81 (d, 1H), 5.25-5.12 (m, 2H), 4.13 (t, 1H) 3.71-3.60 (m, 2H), 1, 45 (s, 9H).

Synthesis route (method reference, The Journal of Medicinal Chemistry, 2014, 57:1531-1542):

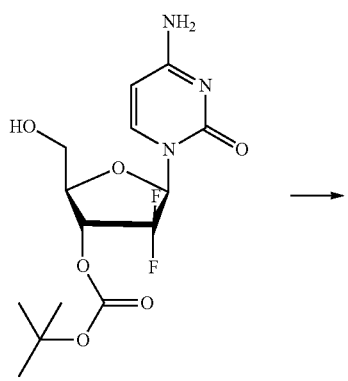

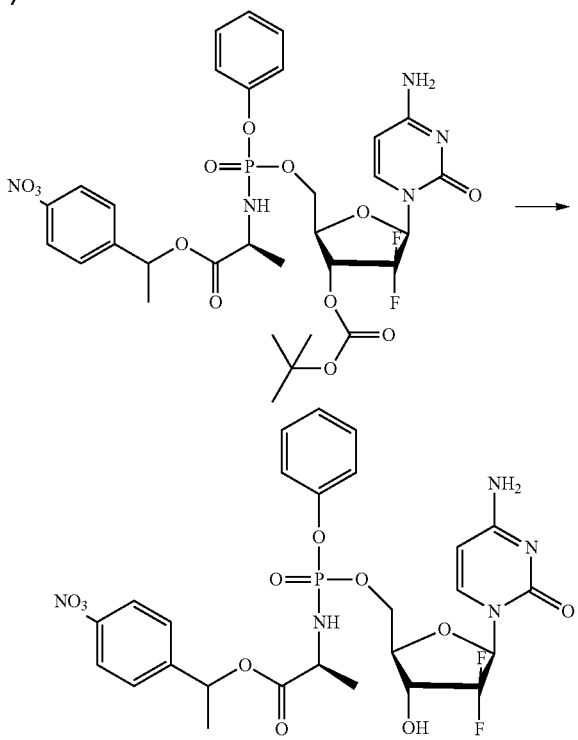

Add 10 mL redistilled dichloromethane into a 100 mL eggplant shape flask, add phosphorus oxychloride (0.2 g, 1.3 mmol) into dichloromethane, place the reaction system at −78° C., add triethylamine (0.13 g, 1.3 mmol) therein, stir for 15 min, then dropwise add a dichloromethane solution (5 mL) of phenol (0.153 g, 1 mmol), react at −78° C. for 1 h after 15 min of dropping, and react at room temperature for 1 h; leave the whole reaction system at −78° C., add 0.23 g (2.3 mmol) triethylamine therein, stir for 15 min, add 10 ml redistilled dichloromethane solution containing 0.275 g (1 mmol) L-alanine-1-(4-nitrophenyl) ethanol ester hydrochloride, and stir for 3 h; add 30 mL redistilled dichloromethane into another 50 mL eggplant shape flask, add 0.29 g (0.8 mmol) 3'-O-(t-butyloxycarboryl) gemcitabine, add 0.2 g (2 mmol) triethylamine, add 2 mL N-methylimidazole, and add the dichloromethane solution into the 100 mL reaction system in the previous flask at room temperature for overnight reaction at room temperature; concentrate the solvent, filter out insoluble substances, wash the filtrate with 3×30 mL water, extract with dichloromethane, concentrate the solvent, stir with 6 mL trifluoroacetic acid and dichloromethane (volume ratio being 1:1) at 0° C. for 4 h, concentrate the solvent, and perform flash column chromatography (volume ratio of dichloromethane:methanol being 20:1); and obtain the compound 001: $^1$H NMR (MeOD, 300 MHz) δ(ppm): 8.22-8.21 (m, 2H), 7.60-7.55 (m, 1H), 7.52-7.51 (m, 2H), 7.41-7.36 (m, 2H), 7.29-7.22 (m, 3H), 6.30-6.25 (m, 1H), 6.04-5.89 (m, 2H), 4.56-4.38 (m, 2H), 4.28-4.21 (m, 1H), 4.15-4.10 (m, 1H), 3.97-3.91 (m, 1H), 1.56-1.55 (m, 3H), 1.38-1.32 (m, 3H).

Compounds 002-021 were synthesized with the same method.

Compound 002

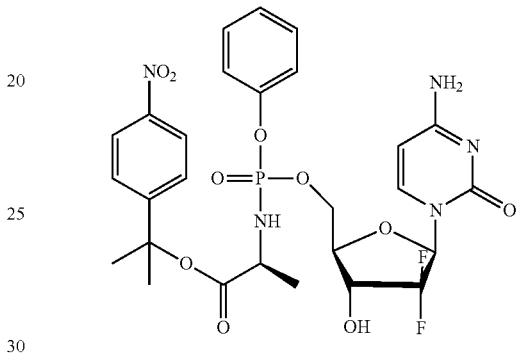

Referring to the method for producing the compound 001, phenol, L-alanine-1-(4-nitrophenyl)-1-methyl ethanol ester hydrochloride, gemcitabine and other raw materials were used for synthesis. $^1$H NMR (MeOD, 300 MHz) δ(ppm): 8.21-8.20 (m, 2H), 7.65-7.64 (m, 2H), 7.54-7.50 (m, 1H), 7.35-7.30 (m, 2H), 7.23-7.18 (m, 3H), 6.25-6.19 (m, 1H), 5.99-5.85 (m, 1H), 4.48-4.37 (m, 2H), 4.23-4.14 (m, 1H), 4.09-4.04 (m, 1H), 3.91-3.84 (m, 4H), 1.74-1.73 (m, 6H), 1.32-1.26 (m, 3H).

Compound 003

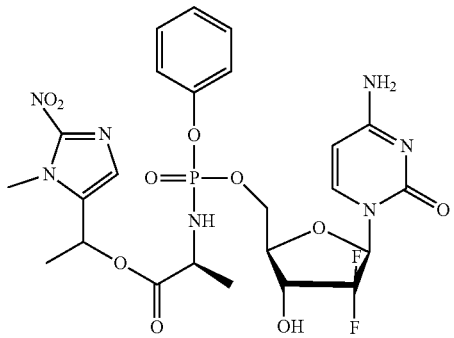

Referring to the method for producing the compound 001, phenol, L-alanine-1-(3-methyl-2-nitro-3H-imidazole-4-yl) ethanol ester hydrochloride, gemcitabine and other raw materials were used for synthesis. $^1$H NMR (MeOD, 300 MHz) δ(ppm): 7.58-7.53 (m, 1H), 7.40-7.33 (m, 2H), 7.30-7.22 (m, 3H), 7.22-7.20 (m, 1H), 6.26-6.23 (m, 1H), 6.02-5.90 (m, 1H), 5.85-5.75 (m, 1H), 4.59-4.41 (m, 2H), 4.20-4.30 (m, 1H), 3.97-3.90 (m, 4H), 1.60-1.59 (m, 3H), 1.34-1.27 (m, 3H).

Compound 004

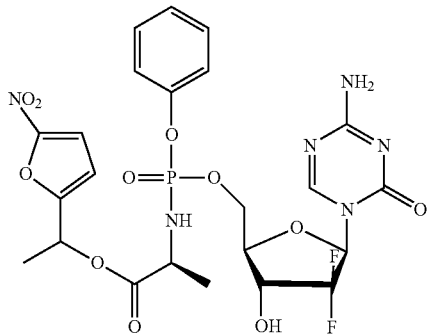

Referring to the method for producing the compound 001, phenol, L-alanine-1-(5-nitro-furan-2-yl) ethanol ester hydrochloride, gemcitabine and other raw materials were used for synthesis. $^1$H NMR (MeOD, 300 MHz) δ(ppm): 7.69 (d, 1H), 7.57-7.52 (m, 1H), 7.38-7.33 (m, 2H), 7.26-7.19 (m, 3H), 6.93 (d, 1H), 6.27-6.21 (m, 1H), 5.97-5.90 (m, 1H), 4.53-4.31 (m, 2H), 4.25-4.18 (m, 1H), 4.12-4.07 (m, 1H), 3.94-3.87 (m, 1H), 1.57-1.56 (m, 3H), 1.35-1.29 (m, 3H).

Compound 005:

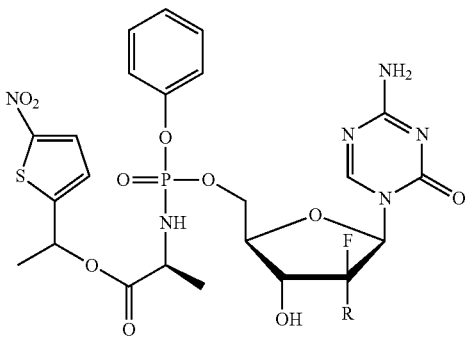

Referring to the method for producing the compound 001, phenol, L-alanine-1-(5-nitro-thiophene-2-yl) ethanol ester hydrochloride, gemcitabine and other raw materials were used for synthesis. $^1$H NMR (MeOD, 300 MHz) δ(ppm): 8.75 (s, 1H), 7.72 (s, 1H), 7.55-7.50 (m, 1H), 7.36-7.31 (m, 2H), 7.24-7.18 (m, 3H), 6.26-6.21 (m, 1H), 6.07-6.01 (m, 1H), 5.90-5.81 (m, 1H), 4.51-4.30 (m, 2H), 4.24-4.16 (m, 1H), 4.10-4.04 (m, 1H), 3.92-3.86 (m, 1H), 1.60-1.59 (m, 3H), 1.32-1.27 (m, 3H).

Compound 006

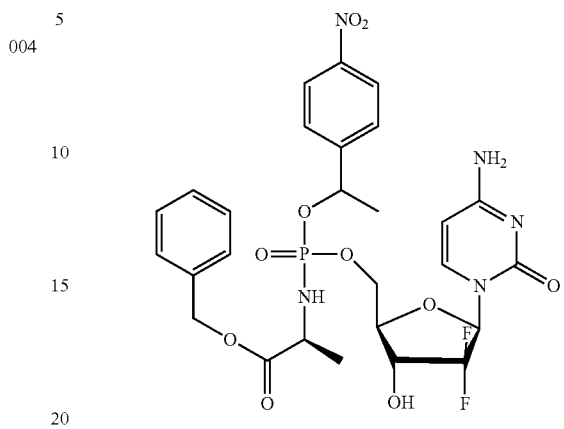

Referring to the method for producing the compound 001, 1-(4-nitrophenyl) ethanol, L-alanine benzyl ester hydrochloride, gemcitabine and other raw materials were used for synthesis. $^1$H NMR (MeOD, 300 MHz) δ(ppm): 8.20-8.18 (m, 2H), 7.64-7.62 (m, 2H), 7.58-7.53 (m, 1H), 7.39-7.34 (m, 5H), 6.28-6.23 (m, 1H), 5.92-5.76 (m, 2H), 5.16-5.10 (m, 2H), 4.54-4.32 (m, 2H), 4.26-4.20 (m, 1H), 4.12-4.06 (m, 1H), 3.95-3.90 (m, 1H), 1.56-1.53 (m, 3H), 1.35-1.30 (m, 3H).

Compound 007:

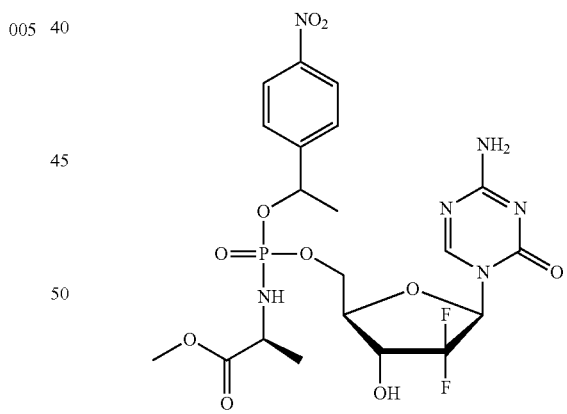

Referring to the method for producing the compound 001, 1-(4-nitrophenyl) ethanol, L-alanine methyl ester hydrochloride, gemcitabine and other raw materials were used for synthesis. $^1$H NMR (MeOD, 300 MHz) δ(ppm): 8.22-8.20 (m, 2H), 7.67-7.65 (m, 2H), 7.60-7.55 (m, 1H), 6.31-6.26 (m, 1H), 5.96-5.80 (m, 2H), 4.57-4.35 (m, 2H), 4.29-4.23 (m, 1H), 4.15-4.09 (m, 1H), 3.97-3.92 (m, 1H), 3.58 (s, 3H), 1.61-1.55 (m, 3H), 1.38-1.33 (m, 3H).

Compound 008

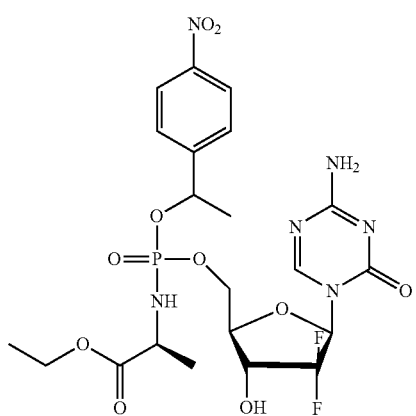

Referring to the method for producing the compound 001, 1-(4-nitrophenyl) ethanol, L-alanine ethyl ester hydrochloride, gemcitabine and other raw materials were used for synthesis. 1H NMR (MeOD, 300 MHz) δ(ppm): 8.19-8.17 (m, 2H), 7.63-7.61 (m, 2H), 7.58-7.52 (m, 1H), 6.26-6.21 (m, 1H), 5.90-5.75 (m, 2H), 4.52-4.30 (m, 2H), 4.24-4.18 (m, 1H), 4.14-4.05 (m, 1H), 3.91-3.75 (m, 3H), 1.55-1.50 (m, 3H), 1.34-1.29 (m, 3H), 1.16-1.12 (m, 3H).

Compound 009:

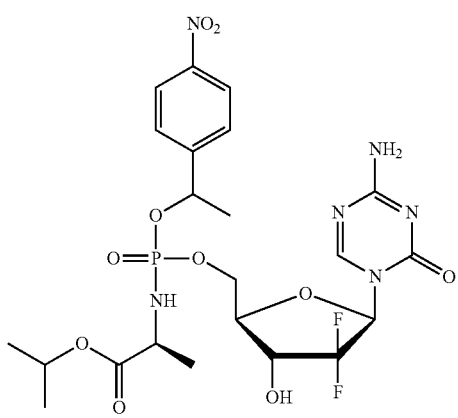

Referring to the method for producing the compound 001, 1-(4-nitrophenyl) ethanol, L-alanine isopropyl ester hydrochloride, gemcitabine and other raw materials were used for synthesis. $^1$H NMR (MeOD, 300 MHz) δ(ppm): 8.21-8.19 (m, 2H), 7.65-7.63 (m, 2H), 7.60-7.56 (m, 1H), 6.29-6.25 (m, 1H), 5.94-5.88 (m, 2H), 5.03-4.97 (m, 1H), 4.55-4.34 (m, 2H), 4.28-4.22 (m, 1H), 4.15-4.10 (m, 1H), 3.98-3.93 (m, 1H), 1.58-1.54 (m, 3H), 1.38-1.31 (m, 3H), 1.26-1.23 (m, 6H).

Compound 010

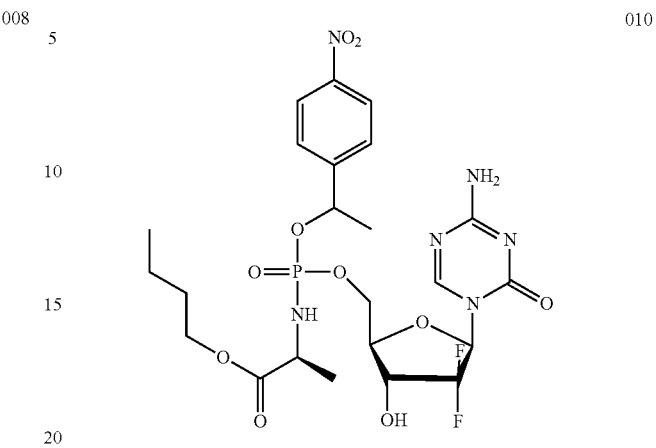

Referring to the method for producing the compound 001, 1-(4-nitrophenyl) ethanol, L-alanine butyl ester hydrochloride, gemcitabine and other raw materials were used for synthesis. $^{1H}$ NMR (MeOD, 300 MHz) δ(ppm): 8.23-8.21 (m, 2H), 7.65-7.63 (m, 2H), 7.62-7.57 (m, 1H), 6.31-6.25 (m, 1H), 5.97-5.79 (m, 2H), 4.58-4.35 (m, 2H), 4.30-4.24 (m, 1H), 4.17-4.12 (m, 1H), 4.00-3.95 (m, 1H), 3.88-3.78 (m, 2H), 1.60-1.20 (m, 10H), 0.85-0.81 (m, 3H).

Compound 011:

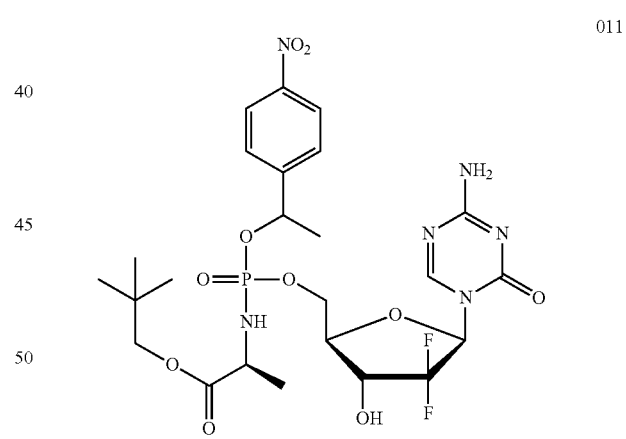

Referring to the method for producing the compound 001, 1-(4-nitrophenyl) ethanol, L-alanine 2,2-dimethyl propyl ester hydrochloride, gemcitabine and other raw materials were used for synthesis. $^{1H}$ NMR (MeOD, 300 MHz) δ(ppm): 8.24-8.22 (m, 2H), 7.66-7.64 (m, 2H), 7.62-7.58 (m, 1H), 6.32-6.27 (m, 1H), 5.99-5.80 (m, 1H), 4.60-4.38 (m, 2H), 4.32-4.26 (m, 1H), 4.18-4.14 (m, 1H), 4.02-3.96 (m, 1H), 3.90-3.80 (m, 2H), 1.62-1.58 (m, 3H), 1.39-1.33 (m, 3H), 1.24-1.21 (m, 9H).

Compound 012

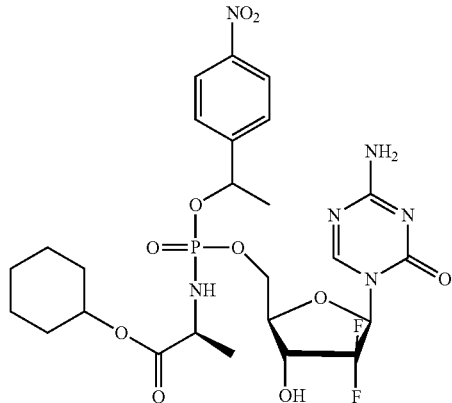

Referring to the method for producing the compound 001, 1-(4-nitrophenyl) ethanol, L-alanine cyclohexyl ester hydrochloride, gemcitabine and other raw materials were used for synthesis. $^1$H NMR (MeOD, 300 MHz) δ(ppm): 8.19-8.17 (m, 2H), 7.63-7.61 (m, 2H), 7.57-7.52 (m, 1H), 6.28-6.23 (m, 1H), 5.94-5.78 (m, 2H), 4.55-4.35 (m, 2H), 4.28-4.20 (m, 2H), 4.15-4.10 (m, 1H), 4.02-3.94 (m, 1H), 1.70-1.52 (m, 5H), 1.39-1.15 (m, 1l 1H).

Compound 014

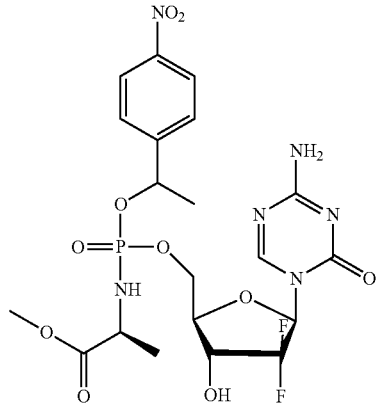

Referring to the method for producing the compound 001, 4-nitrobenzyl alcohol, L-alanine methyl ester hydrochloride, gemcitabine and other raw materials were used for synthesis. $^1$H NMR (MeOD, 300 MHz) δ(ppm): 8.20-8.19 (m, 2H), 7.65-7.63 (m, 2H), 7.59-7.53 (m, 1H), 6.28-6.24 (m, 1H), 5.95-5.90 (m, 1H), 5.14-5.02 (m, 2H), 4.55-4.35 (m, 2H), 4.28-4.21 (m, 1H), 4.15-4.10 (m, 1H), 3.98-3.90 (m, 1H), 3.56 (s, 3H), 1.57-1.53 (m, 3H), 1.36-1.30 (m, 3H).

Compound 013:

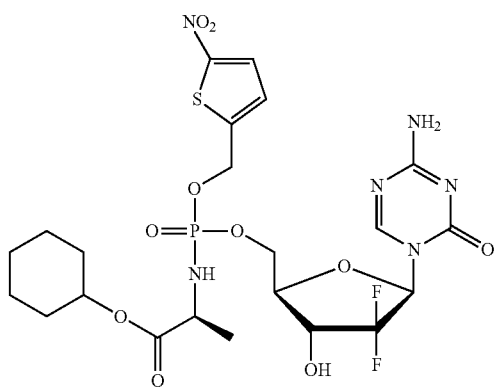

Referring to the method for producing the compound 001, 1-(5-nitrothiophene-2-yl) methanol, L-alanine cyclohexyl ester hydrochloride, gemcitabine and other raw materials were used for synthesis. $^1$H NMR (MeOD, 300 MHz) δ(ppm): 8.08-8.07 (m, 1H), 7.65-7.55 (m, 1H), 7.32-7.31 (m, 1H), 6.30-6.25 (m, 1H), 5.98-5.88 (m, 1H), 5.25-5.07 (m, 3H), 4.55-4.35 (m, 1H), 4.28-4.21 (m, 1H), 4.15-4.10 (m, 1H), 4.04-3.97 (m, 1H), 1.72-1.55 (m, 5H), 1.42-1.18 (m, 11H).

Compound 015:

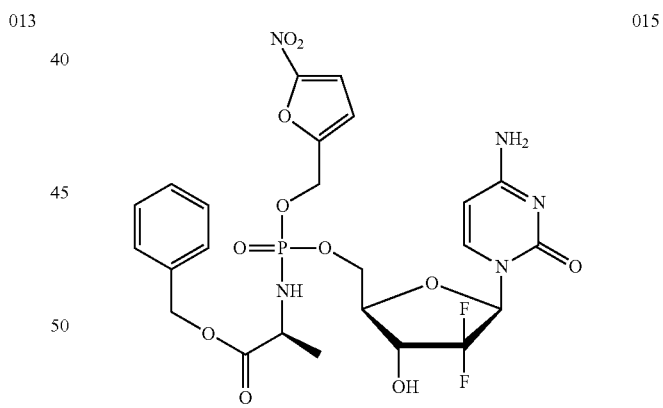

Referring to the method for producing the compound 001, 1-(5-nitrofuran-2-yl) methanol, L-alanine benzyl ester hydrochloride, gemcitabine and other raw materials were used for synthesis. $^1$H NMR (MeOD, 300 MHz) δ(ppm): 7.69-7.68 (m, 1H), 7.65-7.64 (m, 1H), 7.59-7.54 (m, 1H), 7.36-7.29 (m, 5H), 6.29-6.24 (m, 1H), 5.94-5.88 (m, 1H), 5.08-5.03 (m, 2H), 4.57-4.36 (m, 2H), 4.30-4.20 (m, 1H), 4.14-4.09 (m, 1H), 3.97-3.88 (m, 1H), 3.89-3.60 (m, 2H), 1.56-1.51 (m, 3H), 1.35-1.31 (m, 3H).

Compound 016

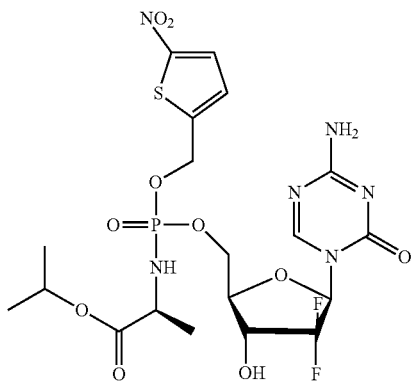

Referring to the method for producing the compound 001, 1-(5-nitrothiophene-2-yl) methanol, L-alanine isopropyl ester hydrochloride, gemcitabine and other raw materials were used for synthesis. $^1$H NMR (MeOD, 300 MHz) δ(ppm): 8.07-8.06 (m, 2H), 7.67-7.55 (m, 1H), 7.31-7.300, 1H), 6.30-6.25 (m, 1H), 5.96-5.88 (m, 1H), 5.22-5.18 (m, 2H), 5.09-4.98 (m, 1H), 4.56-4.35 (m, 1H), 4.32-4.21 (m, 1H), 4.15-4.10 (m, 1H), 3.99-3.90 (m, 1H), 1.38-1.33 (m, 3H) 1.26-1.24 (m, 6H).

Compound 017:

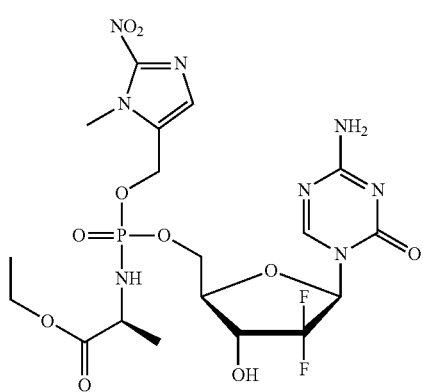

Referring to the method for producing the compound 001, (3-methyl-2-nitro-3H-imidazole-4-yl) methanol, L-alanine ethyl ester hydrochloride, gemcitabine and other raw materials were used for synthesis. $^1$H NMR (MeOD, 300 MHz) δ(ppm): 7.66-7.55 (m, 1H), 7.22-7.21 (m, 1H), 6.29-6.23 (m, 1H), 5.94-5.86 (m, 1H), 4.54-4.31 (m, 2H), 4.26-4.18 (m, 1H), 4.17-4.10 (m, 3H), 3.96-3.70 (m, 3H), 1.36-1.32 (m, 3H), 1.16-1.13 (m, 3H).

Compound 018

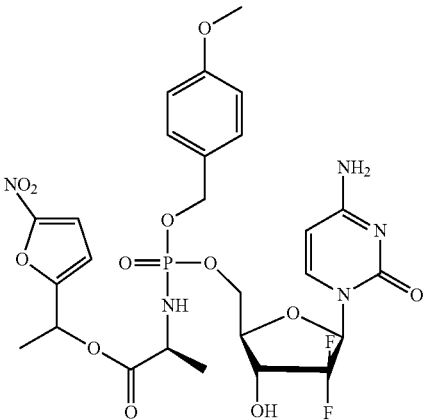

Referring to the method for producing the compound 001, 4-methoxybenzyl alcohol, L-alanine-1-methyl-1-(5-nitro-furan-2-yl) ethanol ester hydrochloride, gemcitabine and other raw materials were used for synthesis. $^1$H NMR (MeOD, 300 MHz) δ(ppm): 7.68-7.66 (m, 1H), 7.61-7.56 (m, 1H), 7.05-7.04 (m, 2H), 6.96-6.94 (m, 2H), 6.32-6.25 (m, 1H), 5.96-5.87 (m, 2H), 5.10-5.03 (m, 2H), 4.57-4.34 (m, 2H), 4.29-4.21 (m, 1H), 4.15-4.09 (m, 1H), 3.98-3.91 (m, 4H), 1.56-1.55 (m, 3H), 1.37-1.32 (m, 3H).

Compound 019:

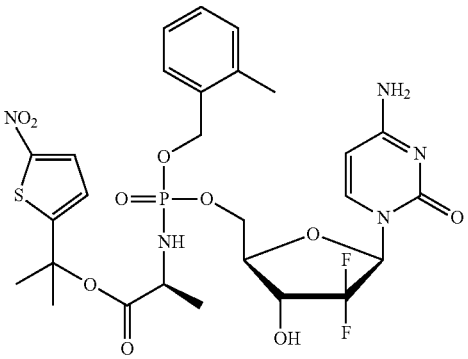

Referring to the method for producing the compound 001, 2-methyl benzyl alcohol, L-alanine-1-methyl-1-(5-nitrothio-phene-2-yl) ethanol ester hydrochloride, gemcitabine and other raw materials were used for synthesis. $^1$H NMR (MeOD, 300 MHz) δ(ppm): 8.73-8.72 (m, 1H), 7.64-7.63 (m, 1H), 7.59-7.54 (m, 1H), 7.37-7.32 (m, 1H), 7.24-7.15 (m, 3H), 6.31-6.23 (m, 1H), 5.95-5.89 (m, 1H), 5.13-5.00 (m, 2H), 4.56-4.32 (m, 2H), 4.28-4.10 (m, 3H), 4.14-4.06 (m, 1H), 3.97-3.90 (m, 1H), 2.37-2.35 (m, 3H), 1.82-1.81 (m, 6H), 1.37-1.30 (m, 6H).

Compound 020

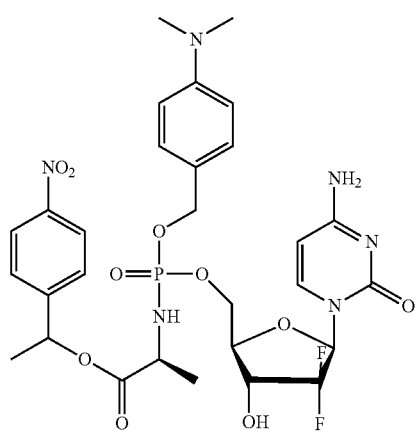

020

Referring to the method for producing the compound 001, 4-N,N-dimethylbenzyl alcohol, L-alanine-1-methyl-1-(5-nitrothiophene-2-yl) ethanol ester hydrochloride, gemcitabine and other raw materials were used for synthesis. $^1$H NMR (MeOD, 300 MHz) δ(ppm): 8.20-8.18 (m, 2H), 7.61-7.56 (m, 1H), 7.50-7.49 (m, 2H), 7.06-6.83 (m, 4H), 6.30-6.21 (m, 1H), 6.02-5.89 (m, 2H), 5.11-4.98 (m, 2H), 4.56-4.32 (m, 2H), 4.29-419 (m, 1H), 4.12-4.06 (m, 1H), 3.96-3.88 (m, 1H), 2.81-2.80 (m, 6H), 1.82-1.81 (m, 6H), 1.35-1.29 (m, 3H).

Compound 021:

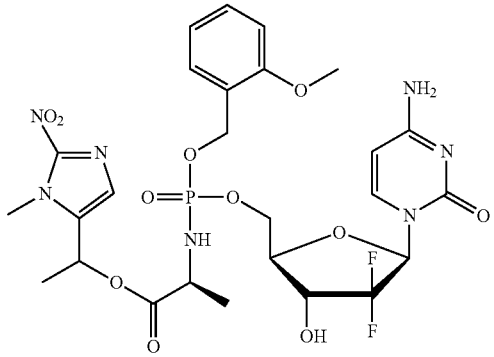

019

Referring to the method for producing the compound 001, 2-methoxybenzyl alcohol, L-alanine-1-(3-methyl-2-nitro-3H-imidazole-4-yl) ethanol ester hydrochloride, gemcitabine and other raw materials were used for synthesis. $^1$H NMR (MeOD, 300 MHz) δ(ppm): 7.55-7.61 (m, 1H), 7.35-7.25 (m, 2H), 7.00-6.92 (m, 2H), 7.20-7.19 (m, 1H), 6.26-6.23 (m, 1H), 5.96-5.84 (m, 1H), 5.04-4.90 (m, 2H), 4.58-4.40 (m, 2H), 4.28-4.17 (m, 1H), 3.95-3.88 (m, 4H), 1.59-1.58 (m, 3H), 1.30-1.20 (m, 3H).

Embodiment 2: Research on In-Vitro Inhibitory Effect of Target Compound on Tumor Cell Proliferation Under Normal Oxygen State and Hypoxic State Take tumor cells in the logarithmic growth phase, add 0.25% pancreatin for digestion for 3 min, use RPMI-1640 containing 10% calf serum for suspension culture of the cells, count the number, adjust cell concentration to $1×10^5$ cells/mL, inoculate to a Top-count dedicated 96-well cell culture plate at 100 μL/well, and incubate at 37° C. and 5% $CO_2$ for 24 h; divide the cells into experimental groups and control groups, and add a target compound solution (0.001 μg/mL, 0.01 μg/mL, 0.1 μg/mL, 1 μg/mL, 10 μg/mL) to the experimental groups, wherein each concentration corresponded to four wells, and the volume of each well was made up to 200 μL; after adding samples, continue to culture for 72 h for each group (for hypoxic groups, continue to culture for 72 h at 5% $CO_2$, 95% $N_2$), add $^3$H-TdR $3×10^5$Bq to each group before culture ended, and measure the CPM (count per minute) value of each well with Top-count; and calculate the median inhibition concentration ($IC_{50}$) of drugs in each experimental group on cell proliferation.

TABLE 1

Median inhibition concentration ($IC_{50}$, μ/mL) of target compound on tumor cell proliferation (72 h) under normal oxygen and hypoxic conditions

| Compound number | $IC_{50}$ normal oxygen (air)/$IC_{50}$ hypoxic (nitrogen) | | |
|---|---|---|---|
| | Human lung adenocarcinoma cell A549 | Human liver cancer HepG2 cell | Human pancreatic adenocarcinoma cell BxPC-3 cell |
| 001 | 1/0.05 | >10/0.3 | >10/0.2 |
| 002 | 2/0.1 | >10/0.2 | >10/0.4 |
| 003 | Not measured | >10/0.4 | Not measured |
| 004 | Not measured | Not measured | >10/0.4 |
| 005 | 2/0.1 | Not measured | Not measured |
| 006 | 2/0.2 | Not measured | >10/0.4 |
| 007 | Not measured | >10/0.5 | >10/0.4 |
| 008 | Not measured | >10/0.3 | >10/0.4 |
| 009 | 2/0.2 | Not measured | >10/0.4 |
| 010 | 2/0.2 | Not measured | Not measured |
| 011 | 2/0.2 | Not measured | Not measured |
| 012 | Not measured | >10/0.5 | >10/0.5 |
| 013 | Not measured | Not measured | >10/0.8 |
| 014 | Not measured | Not measured | >10/0.7 |
| 015 | Not measured | Not measured | >10/0.5 |
| 016 | Not measured | Not measured | >10/0.4 |
| 017 | Not measured | Not measured | >10/0.8 |
| 018 | Not measured | Not measured | >10/0.5 |
| 019 | Not measured | Not measured | >10/0.8 |
| 020 | Not measured | Not measured | >10/0.4 |
| 021 | Not measured | Not measured | >10/0.5 |
| 022 | 0.01/0.01 | 0.4/0.3 | 0.1/0.1 |
| 023 | 0.01/0.01 | 0.4/0.3 | 0.1/0.1 |
| 024 | Not measured | Not measured | >10/>10 |
| Gemcitabine | 0.01/0.01 | 0.2/0.2 | 0.2/0.2 |
| NUC-1031 | 0.01/0.01 | 0.2/0.2 | 0.1/0.1 |

The above experimental results show that gemcitabine, NUC-1031 and compounds 022-024 have no significant difference in in-vitro inhibition on tumor cell proliferation under normal oxygen and hypoxic conditions, and compounds (1-021) of the embodiments of the present invention have significant difference (10-50 times) in in-vitro inhibition on tumor cell proliferation under normal oxygen and hypoxic conditions, indicating that the compounds of the embodiments of the present invention have a stronger cytotoxicity for tumors in hypoxic regions.

Embodiment 3: Growth Inhibition Effect of Target Compound on Orthotopic Transplantation Tumor of Human BxPC-3 Nude Mice Take BxPC-3 human pancreatic cancer cells in the logarithmic growth phase, inoculate subcutaneously on the back of nude mice at a concentration of $5×10^6$ cells·0.2 mL⁻¹·mouse⁻¹, establish a human BxPC-3 nude mice subcutaneous transplantation tumor model, take out after growing into a 1 cm subcutaneous transplantation tumor, remove the central necrotic tissue under an aseptic condition, and select and cut the surrounding healthy tumor tissue into 1 mm³ tissue blocks.

Preparation of surgical orthotopic transplantation model: intraperitoneally anesthetize nude mice with pentobarbital sodium (50 mg/Kg), make a cut beside the left upper rectus abdominis muscle to expose spleen and tail of pancreas, cut open capsula pancreatis, implant a tumor block into the tail of pancreas near splenic artery, and suture the capsula pancreatis.

Administration scheme: model animals were randomly divided into an experimental group (compound 001), a control group, a gemcitabine group and an NUC-1031 group 3 weeks after operation, from the third week after operation, the nude mice were injected intraperitoneally (0.2 mmol/kg, twice per week) for 4 weeks, the nude mice were killed one week after drug withdrawal, and pancreatic tumor tissues were taken and weighed. See FIG. 1 for inhibition effect: growth inhibition effect of target compound on orthotopic transplantation tumor of human BxPC-3 nude mice. After administration, the pancreatic tumor tissue quality of nude mice in the experimental group (compound 001) was significantly lower than those of the gemcitabine group and the NUC-1031 group, indicating a better tumor growth inhibition effect.

Embodiment 4: Growth Inhibition Effect of Target Compound on Subcutaneous Transplantation Tumor of Human BxPC-3 Nude Mice Take BxPC-3 human pancreatic cancer cells in the logarithmic growth phase, inoculate subcutaneously on the back of nude mice at a concentration of 5×10⁶ cells·0.2 mL⁻¹·mouse⁻¹, three weeks later, after the long diameters of the transplanted tumors in nude mice were all ≥5 mm, calculate the similar volume of tumor bodies based on the long diameter and short diameter of the transplanted tumors. Nude mice were divided into 5 groups by a random block design and allocation method according to the tumor volume.

Administration scheme: 50 model animals were randomly divided into a negative control group, a low-dose group (compound 001, 0.1 mmol/kg), a high-dose group (compound 001, 0.4 mmol/kg), a gemcitabine hydrochloride group (0.2 mmol/kg), and a combined administration group (compound 001, 0.1 mmol/kg+ gemcitabine hydrochloride, 0.1 mmol/kg), intraperitoneally injected (twice per week) for 3 weeks, and killed one week after drug withdrawal. At the same time, animal weight was measured and the eye condition of the animal was observed.

Figure 2:
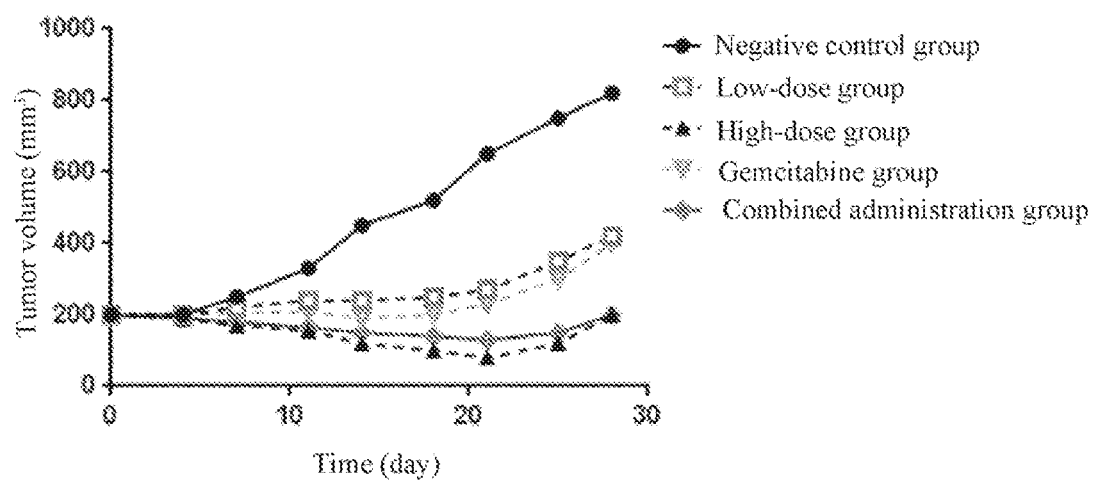
FIG. 2 is a schematic diagram of a growth inhibition effect of a target compound 001 on subcutaneous orthotopic transplantation tumor of human BxPC-3 nude mice. After administration, the pancreatic cancer tumor tissue volume of nude mice in a high-dose group and a low-dose+gemcitabine group was significantly lower than that of a gemcitabine group, indicating a better tumor growth inhibition effect.
Figure 3:
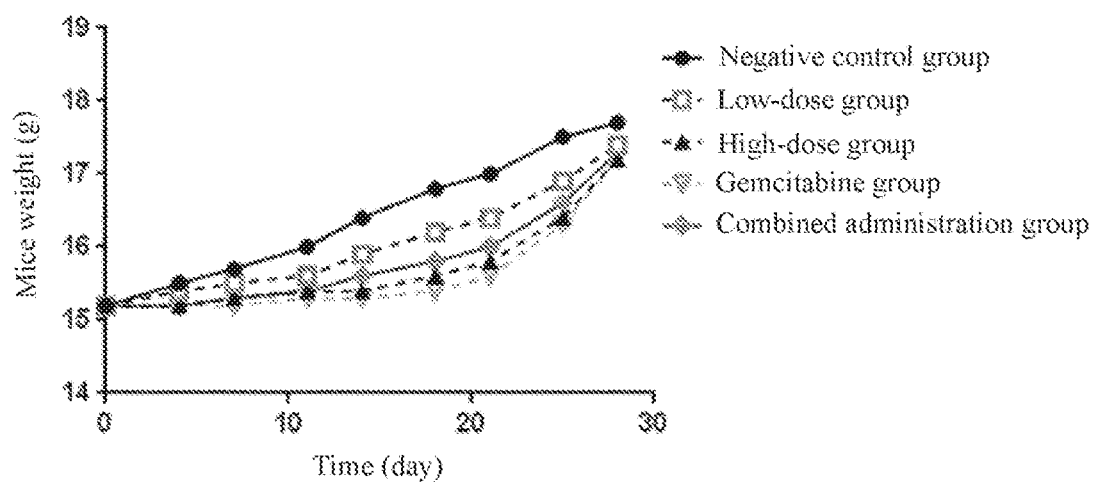
FIG. 3 is a schematic diagram of changes in animal weight when a target compound 001 is used for treating subcutaneous orthotopic transplantation tumor of human BxPC-3 nude mice. Compared with a low-dose group (1 time of the effective dose), the animal weight of a high-dose group (4 times of the effective dose) is not significantly different from that of the low-dose group and a positive control drug gemcitabine group, indicating that the target compound has good safety performance.

See FIG. 2 for inhibition effect and FIG. 3 for weight change: after administration, each group showed a significant tumor growth inhibition effect, and the high-dose group and the combined administration group showed a better therapeutic effect. The weights of nude mice in all experimental groups had no significant difference, but were smaller than those of the control groups.

The above examples are only to illustrate the technical concept and features of the present invention, with the purpose of enabling those familiar with the technology to understand the content of the present invention and implement it accordingly, but do not limit the scope of protection of the present invention. All equivalent changes or modifications made in accordance with the spirit of the present invention should be included within the scope of protection of the present invention.

What is claimed is:

1. A gemcitabine ProTide hypoxic-activated prodrug, wherein the chemical structural formula of the gemcitabine ProTide hypoxic-activated prodrug is:

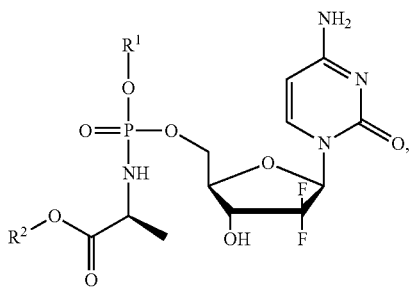

wherein one of R¹ and R² is a hypoxic-activated group of —C(R³R⁴)ArNO₂, the other of R¹ and R² is an alkyl group of 1 to 6 carbon atoms, a phenyl group or —CH₂Ar, R³ and R⁴ are —H or a methyl group, and —Ar is an aromatic ring compound.

2. The gemcitabine ProTide hypoxic-activated prodrug according to claim 1, wherein the structure of R¹ is:

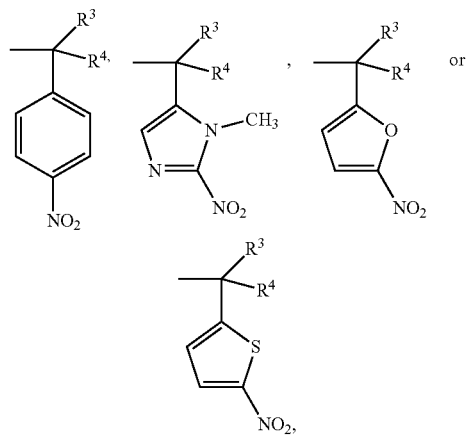

R² is an alkyl or benzyl group of 1 to 6 carbon atoms, R³ is —H or a methyl group, and R⁴ is a methyl group.

3. The gemcitabine ProTide hypoxic-activated prodrug according to claim 1, wherein R¹ is a phenyl group, the structure of R² is:

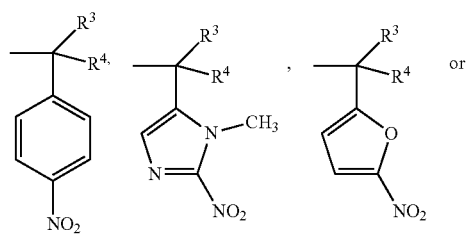

-continued

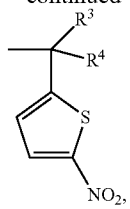

$R^3$ is —H or a methyl group, and $R^4$ is a methyl group.

4. The gemcitabine ProTide hypoxic-activated prodrug according to claim 1, wherein the structure of $R^1$ is:

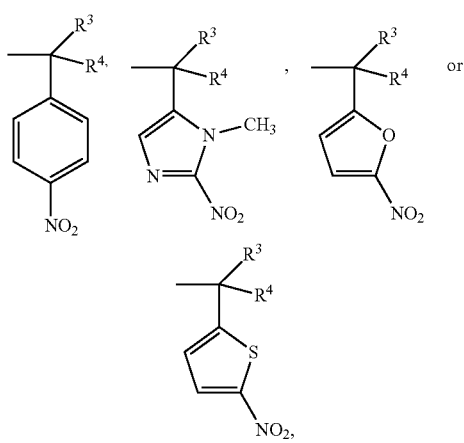

$R^2$ is an alkyl or benzyl group of 1 to 6 carbon atoms, and $R^3$ and $R^4$ are —H.

5. The gemcitabine ProTide hypoxic-activated prodrug according to claim 1, wherein $R^1$ is —CH$_2$Ar, —Ar is a benzene ring with an electron donating group, the structure of $R^2$ is:

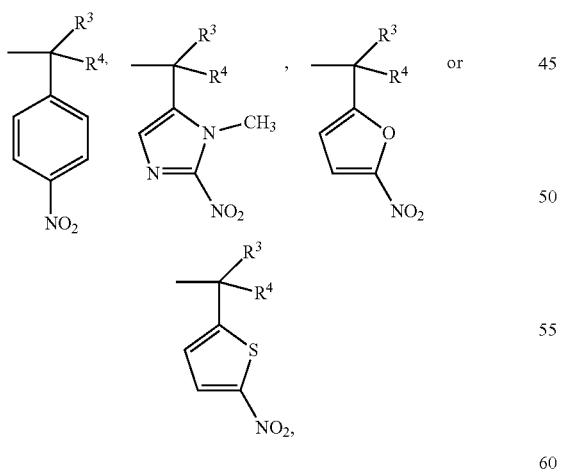

$R^3$ is —H or a methyl group, and $R^4$ is a methyl group.

6. The gemcitabine ProTide hypoxic-activated prodrug according to claim 1, wherein the chemical structural formula of the gemcitabine ProTide hypoxic-activated prodrug is one selected from the group consisting of chemical structural formulas as follows:

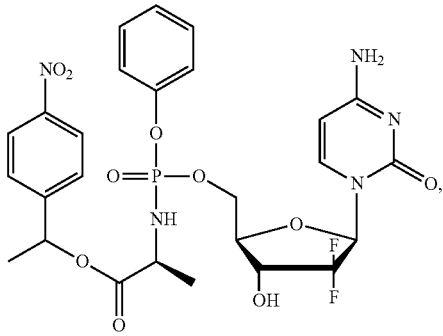

001

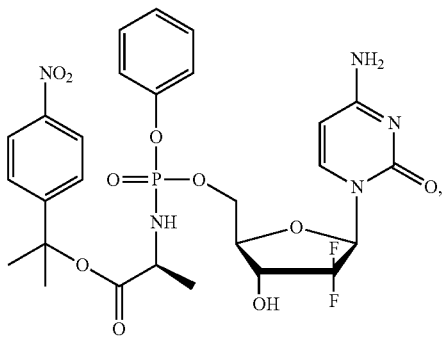

002

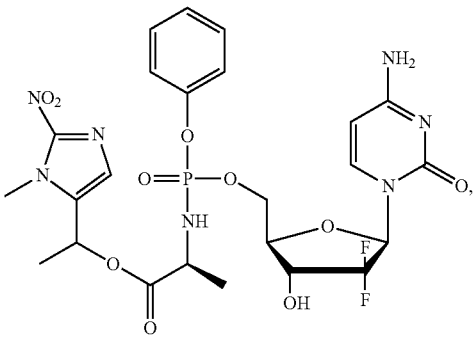

003

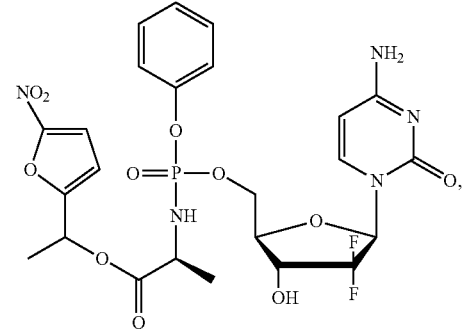

004

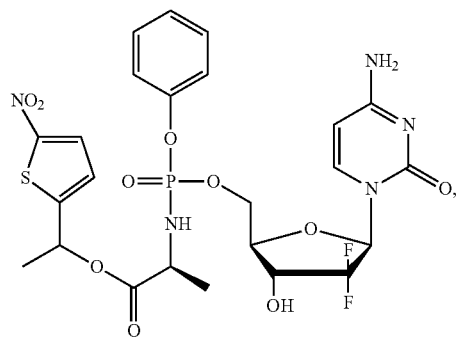
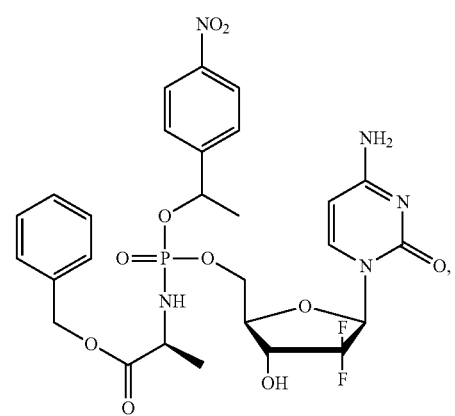
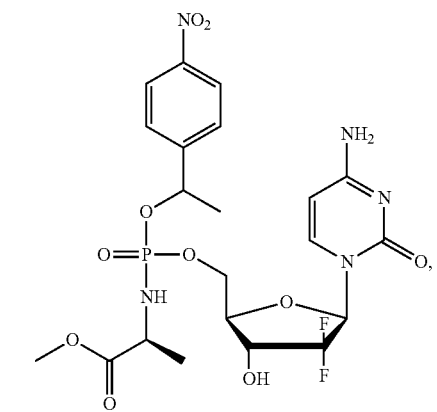
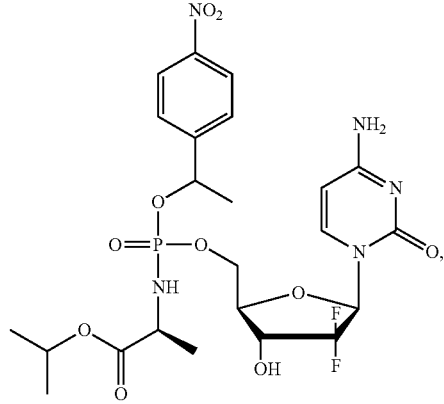
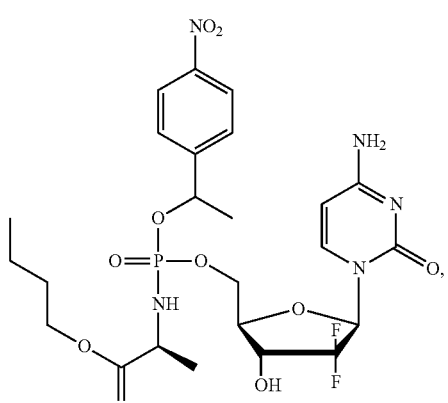
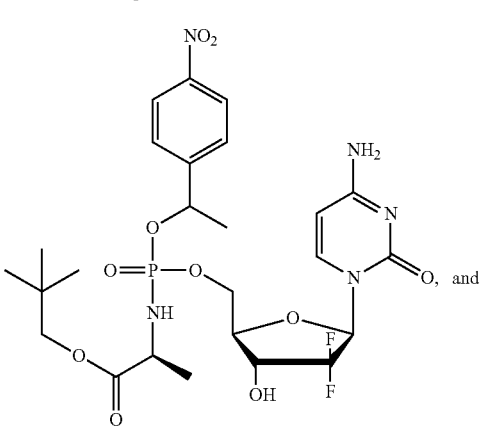
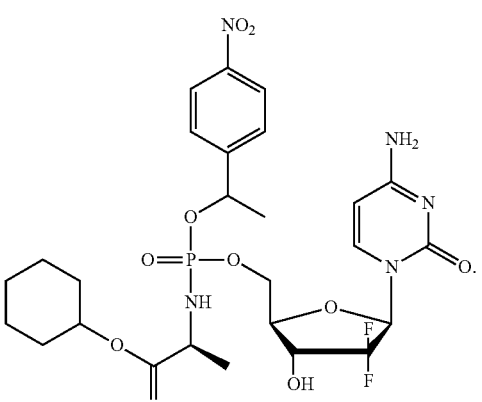

7. The gemcitabine ProTide hypoxic-activated prodrug according to claim 1, wherein the chemical structural formula of the gemcitabine ProTide hypoxic-activated prodrug is one selected from the group consisting of chemical structural formulas as follows:
013
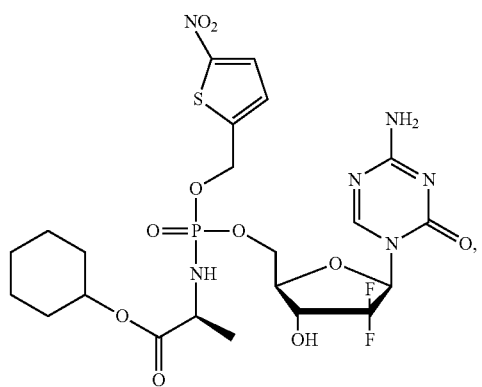
014
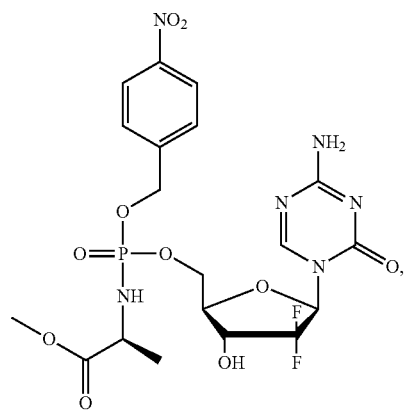
015
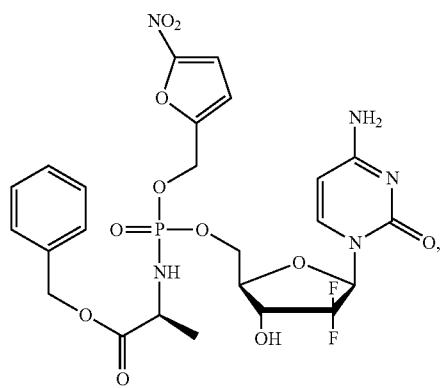
-continued
016
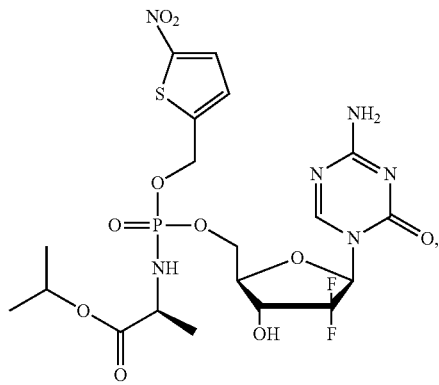
017
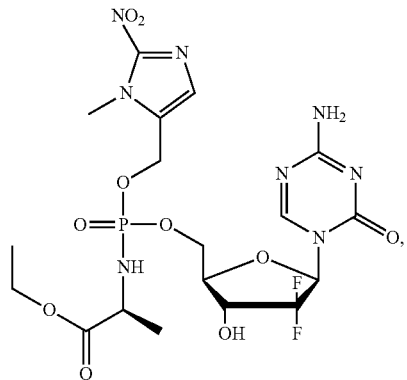
018
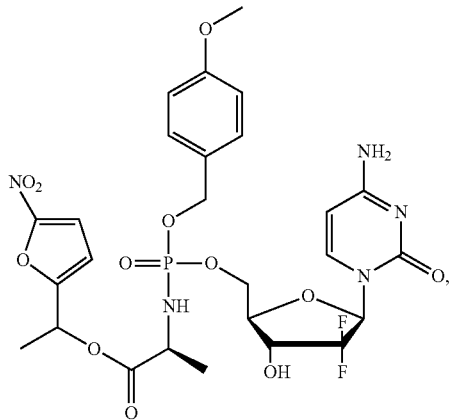
019
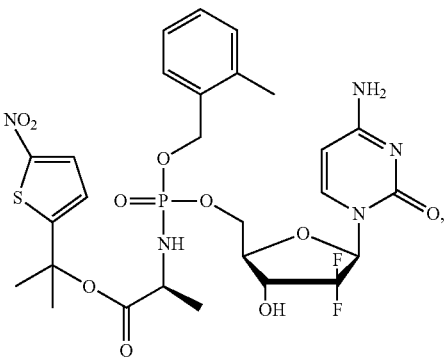

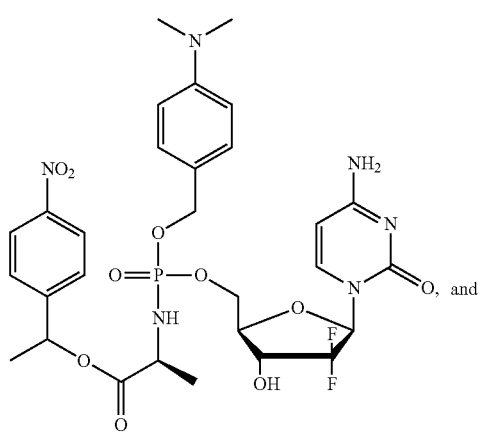

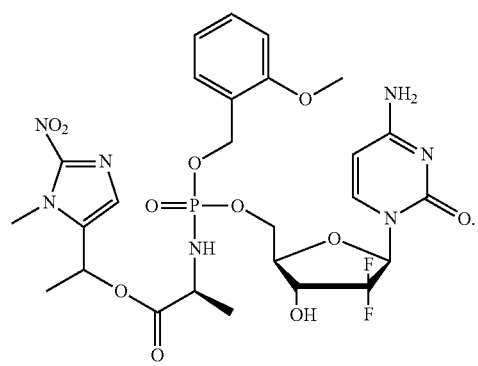

8. A medicament for treating tumors, wherein an effective component of the medicament for treating tumors is the gemcitabine ProTide hypoxic-activated prodrug according to claim 1 or pharmaceutically acceptable salt of the gemcitabine ProTide hypoxic-activated prodrug.

9. The medicament according to claim 8, wherein the structure of $R^1$ is:

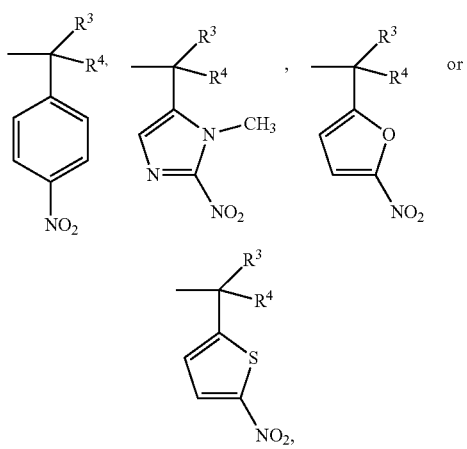

$R^2$ is an alkyl or benzyl group of 1 to 6 carbon atoms, $R^3$ is —H or a methyl group, and $R^4$ is a methyl group.

10. The medicament according to claim 8, wherein $R^1$ is a phenyl group, the structure of $R^2$ is:

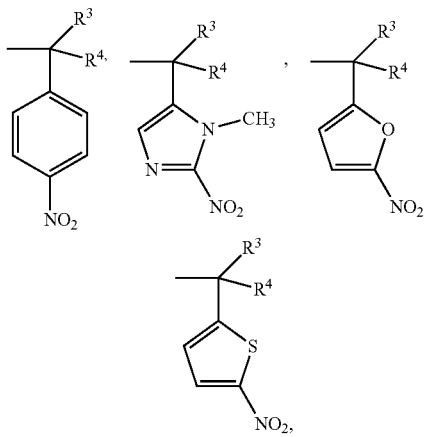

$R^3$ is —H or a methyl group, and $R^4$ is a methyl group.

11. The medicament according to claim 8, wherein the structure of $R^1$ is:

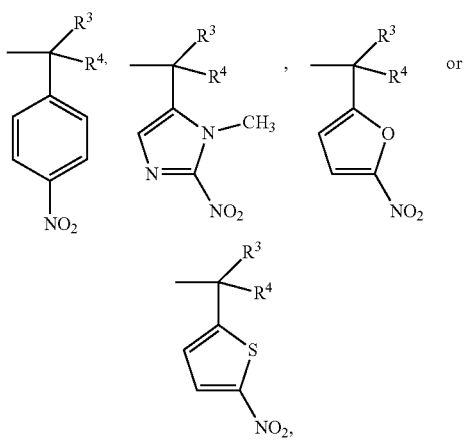

$R^2$ is an alkyl or benzyl group of 1 to 6 carbon atoms, and $R^3$ and $R^4$ are —H.

12. The medicament according to claim 8, wherein $R^1$ is —CH$_2$Ar, —Ar is a benzene ring with an electron donating group, the structure of $R^2$ is:

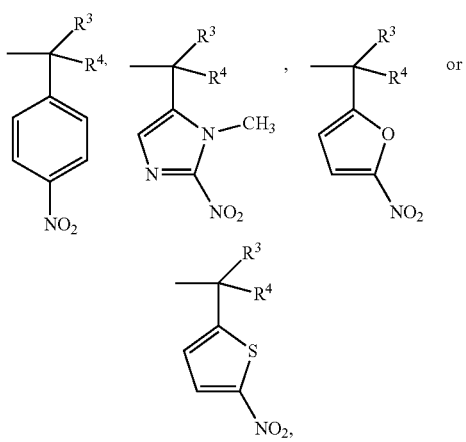

$R^3$ is —H or a methyl group, and $R^4$ is a methyl group.

13. The medicament according to claim 8, wherein the chemical structural formula of the gemcitabine ProTide hypoxic-activated prodrug is one selected from the group consisting of chemical structural formulas as follows:
001
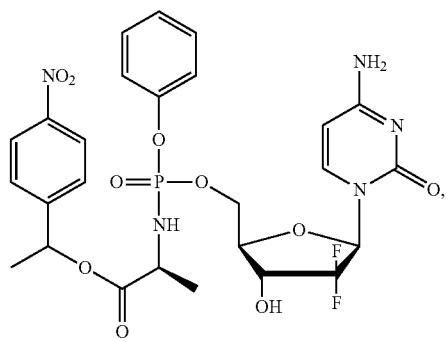
002
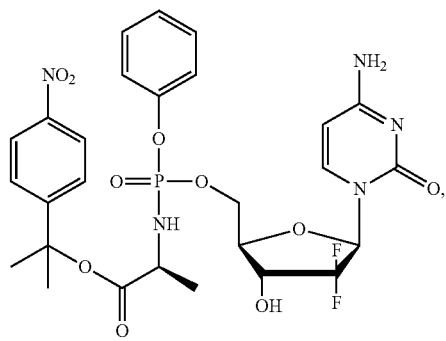
003
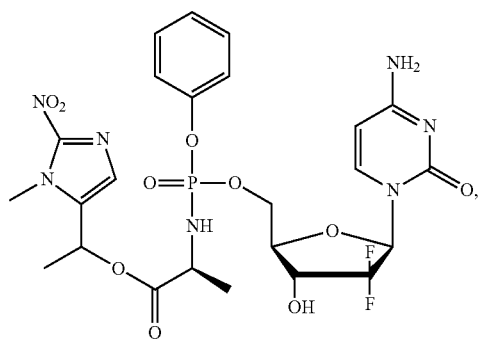
004
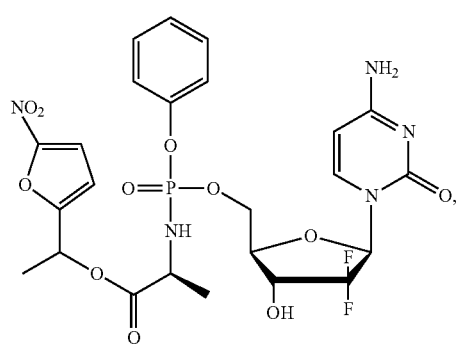
-continued
005
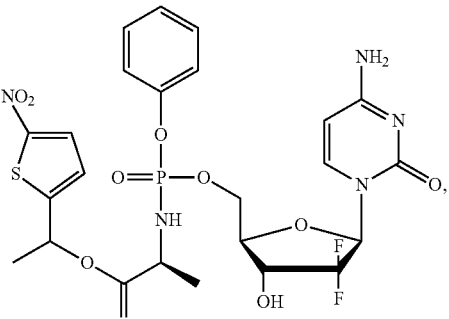
006
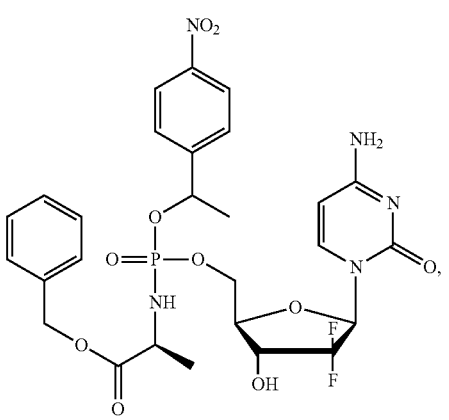
007
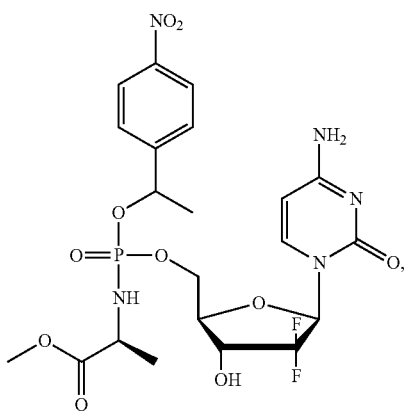
008
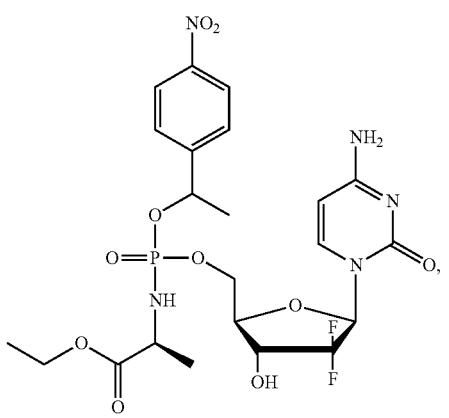

-continued
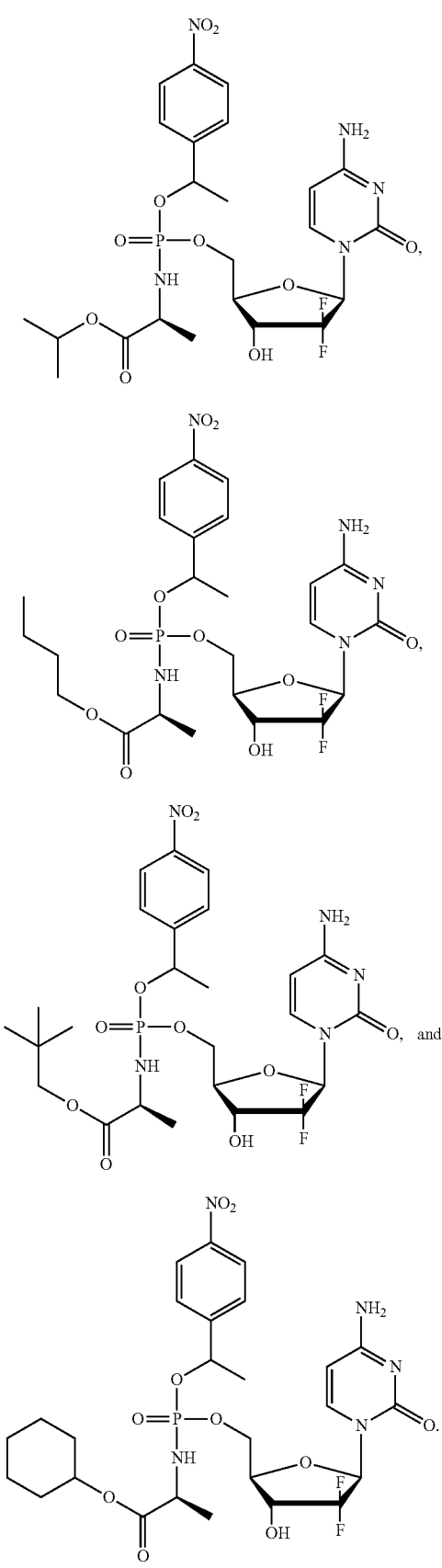
14. The medicament according to claim 8, wherein the chemical structural formula of the gemcitabine ProTide hypoxic-activated prodrug is one selected from the group consisting of chemical structural formulas as follows:

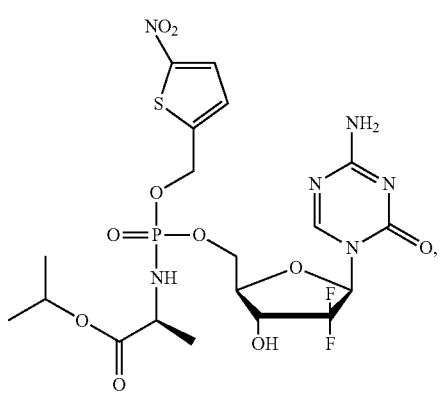
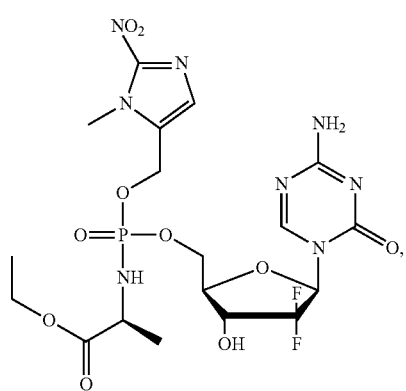
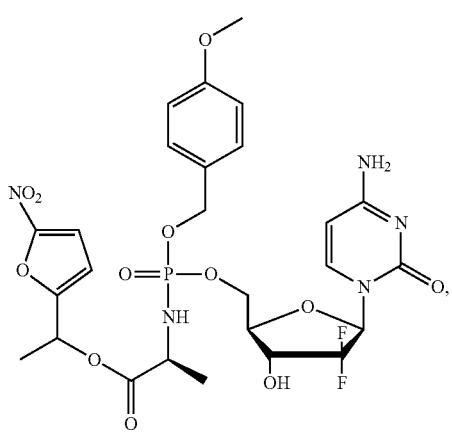
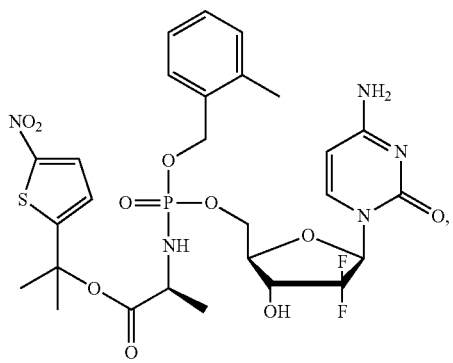
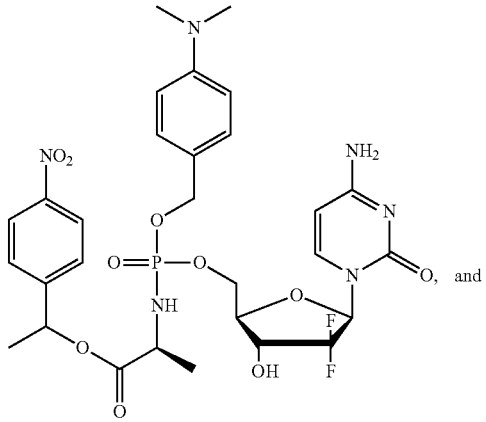
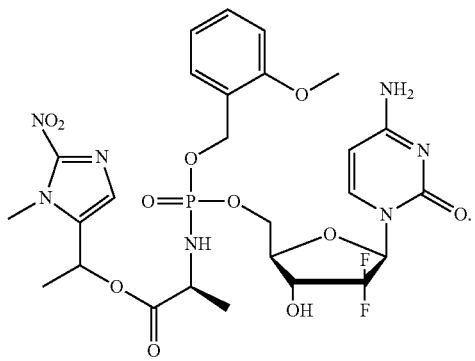
* * * * *